(12) United States Patent
Jenson et al.

(10) Patent No.: US 11,653,945 B2
(45) Date of Patent: May 23, 2023

(54) THROMBECTOMY APPARATUS AND METHOD

(71) Applicant: Walk Vascular, LLC, Irvine, CA (US)

(72) Inventors: Mark L. Jenson, Greenfield, MN (US); William J. Drasler, Minnetonka, MN (US); Joseph M. Thielen, Buffalo, MN (US)

(73) Assignee: Walk Vascular, LLC, Irvine, CA (US)

( * ) Notice: Subject to any disclaimer, the term of this patent is extended or adjusted under 35 U.S.C. 154(b) by 690 days.

(21) Appl. No.: 16/421,649

(22) Filed: May 24, 2019

(65) Prior Publication Data

US 2019/0274704 A1 Sep. 12, 2019

Related U.S. Application Data

(63) Continuation of application No. 15/497,357, filed on Apr. 26, 2017, now Pat. No. 10,314,608, which is a
(Continued)

(51) Int. Cl.
*A61B 17/3203* (2006.01)
*A61B 17/221* (2006.01)
(Continued)

(52) U.S. Cl.
CPC ...... *A61B 17/32037* (2013.01); *A61B 17/221* (2013.01); *A61M 1/84* (2021.05);
(Continued)

(58) Field of Classification Search
CPC ......... A61B 17/32037; A61B 17/3203; A61M 1/84; A61M 25/01
(Continued)

(56) References Cited

U.S. PATENT DOCUMENTS

| 1,114,268 A | 10/1914 | Kells |
| 1,144,268 A | 6/1915 | Vickery |

(Continued)

FOREIGN PATENT DOCUMENTS

| CN | 1120805 A | 4/1996 |
| CN | 201079629 Y | 7/2008 |

(Continued)

OTHER PUBLICATIONS

European Search Report and Written Opinion for Application No. 20164131.3-1122 dated Jun. 24, 2020.
(Continued)

*Primary Examiner* — Wade Miles
*Assistant Examiner* — Bridget E. Rabaglia
(74) *Attorney, Agent, or Firm* — Workman Nydegger; Randy Shen

(57) ABSTRACT

A thrombectomy system may include an elongate shaft that defines a high pressure lumen and a low pressure lumen. The high pressure lumen may terminate near an end of the low pressure lumen. An expandable capture basket may be disposed near the end of the low pressure lumen. A thrombectomy apparatus may include an elongate shaft, an evacuation lumen extending within the elongate shaft and a high pressure lumen extending within the elongate shaft. A capture apparatus may be disposed within a wire lumen that extends within the elongate shaft such that the capture apparatus extends distally from the wire lumen.

20 Claims, 16 Drawing Sheets

Related U.S. Application Data continuation of application No. 14/513,579, filed on Oct. 14, 2014, now Pat. No. 9,662,137, which is a continuation of application No. 12/040,179, filed on Feb. 29, 2008, now Pat. No. 8,900,179, which is a continuation of application No. 12/026,317, filed on Feb. 5, 2008, now Pat. No. 8,430,837.

(60) Provisional application No. 60/888,265, filed on Feb. 5, 2007.

(51) Int. Cl.
 A61M 1/00 (2006.01)
 A61M 25/01 (2006.01)
 A61M 25/09 (2006.01)

(52) U.S. Cl.
 CPC ............ *A61M 25/01* (2013.01); *A61M 25/09* (2013.01); *A61B 2017/2212* (2013.01); *A61M 2025/0183* (2013.01)

(58) Field of Classification Search
 USPC .......................................................... 606/35
 See application file for complete search history.

(56) References Cited

U.S. PATENT DOCUMENTS

| | | |
|---|---|---|
| 1,148,093 A | 7/1915 | Kells |
| 2,804,075 A | 8/1957 | Borden |
| 3,429,313 A | 2/1969 | Romanelli |
| 3,494,363 A | 2/1970 | Jackson |
| 3,589,363 A | 6/1971 | Banko et al. |
| 3,620,650 A | 11/1971 | Shaw |
| 3,631,847 A | 1/1972 | Hobbs |
| 3,693,613 A | 9/1972 | Kelman |
| 3,707,967 A | 1/1973 | Kitrilakis et al. |
| 3,748,435 A | 7/1973 | Reynolds |
| 3,807,401 A | 4/1974 | Bennett et al. |
| 3,818,913 A | 6/1974 | Wallach |
| 3,847,140 A | 11/1974 | Ayella |
| 3,916,892 A | 11/1975 | Latham, Jr. |
| 3,918,453 A | 11/1975 | Leonard |
| 3,930,505 A | 1/1976 | Wallach |
| 3,955,573 A | 5/1976 | Hansen et al. |
| 4,030,503 A | 6/1977 | Clark, III |
| 4,274,411 A | 6/1981 | Dotson, Jr. |
| 4,299,221 A | 11/1981 | Phillips et al. |
| 4,465,470 A | 8/1984 | Kelman |
| 4,573,476 A | 3/1986 | Ruiz |
| 4,574,812 A | 3/1986 | Arkans |
| 4,638,539 A | 1/1987 | Palmer |
| 4,690,672 A | 9/1987 | Veltrup |
| 4,700,705 A | 10/1987 | Kensey et al. |
| 4,702,733 A | 10/1987 | Wright et al. |
| 4,715,853 A | 12/1987 | Prindle |
| 4,728,319 A | 3/1988 | Masch |
| 4,740,203 A | 4/1988 | Hoskins et al. |
| 4,747,821 A | 5/1988 | Kensey et al. |
| 4,747,834 A | 5/1988 | Prindle |
| 4,770,654 A | 9/1988 | Rogers et al. |
| 4,784,157 A | 11/1988 | Halls et al. |
| 4,790,813 A | 12/1988 | Kensey |
| 4,832,685 A | 5/1989 | Haines |
| 4,842,579 A | 6/1989 | Shiber |
| 4,854,325 A | 8/1989 | Stevens |
| 4,857,046 A | 8/1989 | Stevens et al. |
| 4,883,458 A | 11/1989 | Shiber |
| 4,883,467 A | 11/1989 | Franetzki et al. |
| 4,886,490 A | 12/1989 | Shiber |
| 4,886,507 A | 12/1989 | Patton et al. |
| 4,894,051 A | 1/1990 | Shiber |
| 4,898,574 A | 2/1990 | Uchiyama et al. |
| 4,957,482 A | 9/1990 | Shiber |
| 4,979,939 A | 12/1990 | Shiber |
| 4,998,919 A | 3/1991 | Schnepp-Pesch et al. |
| 5,002,553 A | 3/1991 | Shiber |
| 5,007,896 A | 4/1991 | Shiber |
| 5,011,468 A | 4/1991 | Lundquist et al. |
| 5,011,488 A | 4/1991 | Ginsburg |
| 5,024,651 A | 6/1991 | Shiber |
| 5,055,109 A | 10/1991 | Gould et al. |
| 5,057,098 A | 10/1991 | Zelman |
| 5,064,428 A | 11/1991 | Cope et al. |
| 5,073,164 A | 12/1991 | Hollister et al. |
| 5,073,168 A | 12/1991 | Danforth |
| 5,074,841 A | 12/1991 | Ademovic et al. |
| 5,078,722 A | 1/1992 | Stevens |
| 5,091,656 A | 2/1992 | Gahn |
| 5,125,893 A | 6/1992 | Dryden |
| 5,129,887 A | 7/1992 | Euteneuer et al. |
| 5,135,482 A | 8/1992 | Neracher |
| 5,135,531 A | 8/1992 | Shiber |
| 5,158,564 A | 10/1992 | Schnepp-Pesch et al. |
| 5,163,433 A | 11/1992 | Kagawa et al. |
| 5,195,954 A | 3/1993 | Schnepp-Pesch et al. |
| 5,197,795 A | 3/1993 | Mudrovich |
| 5,197,951 A | 3/1993 | Mahurkar |
| 5,234,407 A | 8/1993 | Teirstein et al. |
| 5,242,404 A | 9/1993 | Conley et al. |
| 5,243,997 A | 9/1993 | Uflacker et al. |
| 5,248,297 A | 9/1993 | Takase |
| 5,254,085 A | 10/1993 | Cleveland |
| 5,261,877 A | 11/1993 | Fine et al. |
| 5,284,486 A | 2/1994 | Kotula et al. |
| 5,290,247 A | 3/1994 | Crittenden |
| 5,306,244 A | 4/1994 | Shiber |
| 5,312,427 A | 5/1994 | Shturman |
| 5,318,518 A | 6/1994 | Plechinger et al. |
| 5,318,529 A | 6/1994 | Kontos |
| 5,320,604 A | 6/1994 | Walker et al. |
| 5,322,504 A | 6/1994 | Doherty et al. |
| 5,324,263 A | 6/1994 | Kraus et al. |
| 5,325,868 A | 7/1994 | Kimmelstiel |
| 5,327,906 A | 7/1994 | Fideler |
| 5,334,211 A | 8/1994 | Shiber |
| 5,342,293 A | 8/1994 | Zanger |
| 5,342,306 A | 8/1994 | Don Michael |
| 5,356,375 A | 10/1994 | Higley |
| 5,368,555 A | 11/1994 | Sussman et al. |
| 5,370,609 A | 12/1994 | Drasler et al. |
| 5,385,562 A | 1/1995 | Adams et al. |
| 5,389,072 A | 2/1995 | Imran |
| 5,392,778 A | 2/1995 | Horzewski |
| 5,395,315 A | 3/1995 | Griep |
| 5,403,274 A | 4/1995 | Cannon |
| 5,403,276 A | 4/1995 | Schechter et al. |
| 5,413,561 A | 5/1995 | Fischell et al. |
| 5,419,772 A | 5/1995 | Teitz et al. |
| 5,421,826 A | 6/1995 | Crocker et al. |
| 5,429,601 A | 7/1995 | Conley et al. |
| 5,443,078 A | 8/1995 | Uflacker |
| 5,443,443 A | 8/1995 | Shiber |
| 5,476,450 A | 12/1995 | Ruggio |
| 5,478,331 A | 12/1995 | Heflin et al. |
| 5,486,183 A | 1/1996 | Middleman et al. |
| 5,490,837 A | 2/1996 | Blaeser et al. |
| 5,496,267 A | 3/1996 | Drasler et al. |
| 5,507,738 A | 4/1996 | Ciervo |
| 5,524,180 A | 6/1996 | Wang et al. |
| 5,524,635 A | 6/1996 | Uflacker et al. |
| 5,527,274 A | 6/1996 | Zakko |
| 5,536,242 A | 7/1996 | Willard et al. |
| 5,538,002 A | 7/1996 | Boussignac et al. |
| 5,562,692 A | 10/1996 | Bair |
| 5,569,275 A | 10/1996 | Kotula et al. |
| 5,577,674 A | 11/1996 | Altonji et al. |
| 5,605,545 A | 2/1997 | Nowosielski et al. |
| 5,606,968 A | 3/1997 | Mang |
| 5,624,394 A | 4/1997 | Barnitz et al. |
| 5,626,563 A | 5/1997 | Dodge et al. |
| 5,634,475 A | 6/1997 | Wolvek |
| 5,647,847 A | 7/1997 | LaFontaine et al. |
| 5,653,696 A | 8/1997 | Shiber |

(56) References Cited

U.S. PATENT DOCUMENTS

| | | |
|---|---|---|
| 5,660,180 A | 8/1997 | Malinowski et al. |
| 5,669,876 A | 9/1997 | Schechter et al. |
| 5,695,507 A | 12/1997 | Auth et al. |
| 5,709,661 A | 1/1998 | Van Egmond et al. |
| 5,713,849 A | 2/1998 | Bosma et al. |
| 5,713,851 A | 2/1998 | Boudewijn et al. |
| 5,713,878 A | 2/1998 | Moutafis et al. |
| 5,730,717 A | 3/1998 | Gelbfish |
| 5,735,535 A | 4/1998 | McCombs et al. |
| 5,766,191 A | 6/1998 | Trerotola |
| 5,772,674 A | 6/1998 | Nakhjavan |
| 5,785,685 A | 7/1998 | Kugler et al. |
| 5,795,322 A | 8/1998 | Boudewijn |
| 5,795,332 A | 8/1998 | Lucas et al. |
| 5,810,770 A | 9/1998 | Chin et al. |
| 5,827,229 A | 10/1998 | Auth et al. |
| 5,827,243 A | 10/1998 | Palestrant |
| 5,833,644 A | 11/1998 | Zadno-Azizi et al. |
| 5,843,022 A | 12/1998 | Willard et al. |
| 5,843,051 A | 12/1998 | Adams et al. |
| 5,853,384 A | 12/1998 | Bair |
| 5,855,567 A | 1/1999 | Reesemann |
| 5,868,702 A | 2/1999 | Stevens et al. |
| 5,871,462 A | 2/1999 | Yoder et al. |
| 5,876,414 A | 3/1999 | Straub |
| 5,885,238 A | 3/1999 | Stevens et al. |
| 5,885,244 A | 3/1999 | Leone et al. |
| 5,893,857 A | 4/1999 | Shturman et al. |
| 5,895,398 A | 4/1999 | Wensel et al. |
| 5,895,399 A | 4/1999 | Barbut et al. |
| 5,908,395 A | 6/1999 | Stalker et al. |
| 5,910,252 A | 6/1999 | Truitt et al. |
| 5,911,722 A | 6/1999 | Adler et al. |
| 5,916,192 A | 6/1999 | Nita et al. |
| 5,921,958 A | 7/1999 | Ressemann et al. |
| 5,938,645 A | 8/1999 | Gordon |
| 5,941,871 A | 8/1999 | Adams et al. |
| 5,944,686 A | 8/1999 | Patterson et al. |
| 5,957,901 A | 9/1999 | Mottola et al. |
| 5,989,210 A | 11/1999 | Morris et al. |
| 5,989,271 A | 11/1999 | Bonnette et al. |
| 6,001,112 A | 12/1999 | Taylor |
| 6,007,513 A | 12/1999 | Anis et al. |
| 6,019,728 A | 2/2000 | Iwata et al. |
| 6,022,336 A | 2/2000 | Zandna-Azizi et al. |
| 6,027,460 A | 2/2000 | Shturman |
| 6,080,170 A | 6/2000 | Nash et al. |
| 6,090,118 A | 7/2000 | McGuckin, Jr. |
| 6,096,001 A | 8/2000 | Drasler et al. |
| 6,126,635 A | 10/2000 | Simpson et al. |
| 6,129,697 A | 10/2000 | Drasler et al. |
| 6,129,698 A | 10/2000 | Beck |
| 6,146,355 A | 11/2000 | Biggs |
| 6,146,396 A | 11/2000 | Konya et al. |
| 6,152,909 A | 11/2000 | Bagaoisan et al. |
| 6,156,046 A | 12/2000 | Passafaro et al. |
| 6,159,230 A | 12/2000 | Samuels |
| 6,165,188 A | 12/2000 | Saadat et al. |
| 6,176,844 B1 | 1/2001 | Lee |
| 6,179,809 B1 | 1/2001 | Khairkhahan et al. |
| 6,179,851 B1 | 1/2001 | Barbut et al. |
| 6,183,432 B1 | 2/2001 | Milo |
| 6,190,357 B1 | 2/2001 | Ferrari et al. |
| 6,196,989 B1 | 3/2001 | Padget et al. |
| 6,206,898 B1 | 3/2001 | Honeycutt et al. |
| 6,216,573 B1 | 4/2001 | Moutafis et al. |
| 6,224,570 B1 | 5/2001 | Le et al. |
| 6,238,405 B1 | 5/2001 | Findlay et al. |
| 6,258,061 B1 | 7/2001 | Drasler et al. |
| 6,283,719 B1 | 9/2001 | Frantz et al. |
| 6,293,960 B1 | 9/2001 | Ken |
| 6,331,171 B1 | 12/2001 | Cohen |
| 6,348,040 B1 | 2/2002 | Stalker et al. |
| 6,375,635 B1 | 4/2002 | Moutafis et al. |
| 6,423,032 B2 | 7/2002 | Parodi |
| 6,440,148 B1 | 8/2002 | Shiber |
| 6,454,741 B1 | 9/2002 | Muni et al. |
| 6,454,775 B1 | 9/2002 | Demarais et al. |
| 6,471,683 B2 | 10/2002 | Drasler et al. |
| 6,481,439 B1 | 11/2002 | Lewis et al. |
| 6,488,672 B1 | 12/2002 | Dance et al. |
| 6,508,823 B1 | 1/2003 | Gonon |
| 6,533,772 B1 | 3/2003 | Sherts et al. |
| 6,544,209 B1 | 4/2003 | Drasler et al. |
| 6,544,231 B1 | 4/2003 | Palmer et al. |
| 6,551,302 B1 | 4/2003 | Rosinko et al. |
| 6,554,794 B1 | 4/2003 | Mueller et al. |
| 6,554,799 B1 | 4/2003 | Hatamura et al. |
| 6,558,366 B1 | 5/2003 | Drasler et al. |
| 6,558,401 B1 | 5/2003 | Azizi |
| 6,569,147 B1 | 5/2003 | Evans et al. |
| 6,569,148 B2 | 5/2003 | Bagaoisan et al. |
| 6,572,578 B1 | 6/2003 | Blanchard |
| 6,579,270 B2 | 6/2003 | Sussman et al. |
| 6,585,705 B1 | 7/2003 | Maginot et al. |
| 6,599,271 B1 | 7/2003 | Easley |
| 6,615,835 B1 | 9/2003 | Cise et al. |
| 6,616,679 B1 | 9/2003 | Khorsavi et al. |
| 6,622,367 B1 | 9/2003 | Bolduc et al. |
| 6,623,495 B2 | 9/2003 | Findlay et al. |
| 6,635,034 B1 | 10/2003 | Cosmescu |
| 6,635,070 B2 | 10/2003 | Leeflang et al. |
| 6,638,235 B2 | 10/2003 | Miller et al. |
| 6,652,546 B1 | 11/2003 | Nash et al. |
| 6,652,548 B2 | 11/2003 | Evans et al. |
| 6,663,613 B1 | 12/2003 | Evans et al. |
| 6,669,710 B2 | 12/2003 | Moutafis et al. |
| 6,676,637 B1 | 1/2004 | Bonnette et al. |
| 6,702,830 B1 | 3/2004 | Demarais et al. |
| 6,719,717 B1 | 4/2004 | Johnson et al. |
| 6,723,081 B1 | 4/2004 | Hektner |
| 6,726,675 B1 | 4/2004 | Beyar |
| 6,752,800 B1 | 6/2004 | Winston et al. |
| 6,755,803 B1 | 6/2004 | Le et al. |
| 6,755,812 B2 | 6/2004 | Peterson et al. |
| 6,790,215 B2 | 9/2004 | Findlay et al. |
| 6,805,684 B2 | 10/2004 | Bonnette et al. |
| 6,818,001 B2 | 11/2004 | Wulfman et al. |
| 6,824,545 B2 | 11/2004 | Sepetka et al. |
| 6,824,550 B1 | 11/2004 | Noriega et al. |
| 6,830,577 B2 | 12/2004 | Nash et al. |
| 6,875,193 B1 | 4/2005 | Bonnette et al. |
| 6,899,712 B2 | 5/2005 | Moutafis et al. |
| 6,926,726 B2 | 8/2005 | Drasler et al. |
| 6,929,633 B2 | 8/2005 | Evans et al. |
| 6,936,056 B2 | 8/2005 | Nash et al. |
| 6,945,977 B2 | 9/2005 | Demarais et al. |
| 6,958,059 B2 | 10/2005 | Zadno-Azizi |
| 6,984,239 B1 | 1/2006 | Drasler et al. |
| 6,986,778 B2 | 1/2006 | Zadno-Azizi |
| 6,991,625 B1 | 1/2006 | Gately et al. |
| 7,008,434 B2 | 3/2006 | Kurz et al. |
| 7,044,958 B2 | 5/2006 | Douk et al. |
| 7,108,704 B2 | 9/2006 | Trerotola |
| 7,122,017 B2 | 10/2006 | Moutafis et al. |
| 7,220,269 B1 | 5/2007 | Ansel et al. |
| 7,232,452 B2 | 6/2007 | Adams et al. |
| 7,374,560 B2 | 5/2008 | Ressemann et al. |
| 7,431,711 B2 | 10/2008 | Moutafis et al. |
| 7,479,147 B2 | 1/2009 | Honeycutt et al. |
| 7,481,222 B2 | 1/2009 | Reissmann |
| 7,588,033 B2 | 9/2009 | Wondka |
| 7,591,816 B2 | 9/2009 | Wang et al. |
| 7,604,612 B2 | 10/2009 | Ressemann et al. |
| 7,615,042 B2 | 11/2009 | Beyar et al. |
| 7,621,886 B2 | 11/2009 | Burnett |
| 7,654,996 B2 | 2/2010 | Lynn |
| 7,655,016 B2 | 2/2010 | Demarais et al. |
| 7,666,161 B2 | 2/2010 | Nash et al. |
| 7,699,804 B2 | 4/2010 | Barry et al. |
| 7,713,235 B2 | 5/2010 | Torrance et al. |
| 7,717,685 B2 | 5/2010 | Moutafis et al. |
| 7,717,898 B2 | 5/2010 | Gately et al. |
| 7,736,355 B2 | 6/2010 | Itou et al. |

(56) References Cited

U.S. PATENT DOCUMENTS

| | | |
|---|---|---|
| 7,753,868 B2 | 7/2010 | Hoffa |
| 7,753,880 B2 | 7/2010 | Malackowski |
| 7,766,894 B2 | 8/2010 | Weitzner et al. |
| 7,776,005 B2 | 8/2010 | Haggstrom et al. |
| 7,798,996 B1 | 9/2010 | Haddad et al. |
| 7,798,999 B2 | 9/2010 | Bailey et al. |
| 7,806,864 B2 | 10/2010 | Haddad et al. |
| 7,833,239 B2 | 11/2010 | Nash |
| 7,842,055 B2 | 11/2010 | Pintor et al. |
| 7,846,175 B2 | 12/2010 | Bonnette et al. |
| 7,862,575 B2 | 1/2011 | Tal |
| 7,867,192 B2 | 1/2011 | Bowman et al. |
| 7,875,004 B2 | 1/2011 | Yodfat et al. |
| 7,879,022 B2 | 2/2011 | Bonnette et al. |
| 7,887,510 B2 | 2/2011 | Karpowicz et al. |
| 7,905,710 B2 | 3/2011 | Wang et al. |
| 7,909,801 B2 | 3/2011 | Hinchliffe |
| 7,909,810 B2 | 3/2011 | Noone |
| 7,914,482 B2 | 3/2011 | Urich et al. |
| 7,914,549 B2 | 3/2011 | Morsi |
| 7,918,654 B2 | 4/2011 | Adahan |
| 7,918,822 B2 | 4/2011 | Kumar et al. |
| 7,918,835 B2 | 4/2011 | Callahan et al. |
| 7,935,077 B2 | 5/2011 | Thor et al. |
| 7,951,073 B2 | 5/2011 | Freed |
| 7,951,107 B2 | 5/2011 | Staid et al. |
| 7,951,112 B2 | 5/2011 | Patzer |
| 7,959,603 B2 | 6/2011 | Wahr et al. |
| 7,959,608 B2 | 6/2011 | Nash et al. |
| 7,976,528 B2 | 7/2011 | Nash et al. |
| 7,981,128 B2 | 7/2011 | To et al. |
| 7,981,129 B2 | 7/2011 | Nash et al. |
| 7,998,114 B2 | 8/2011 | Lombardi |
| 8,007,490 B2 | 8/2011 | Schaeffer et al. |
| 8,012,766 B2 | 9/2011 | Graham |
| 8,021,351 B2 | 9/2011 | Boldenow et al. |
| 8,034,018 B2 | 10/2011 | Lutwyche |
| 8,043,312 B2 | 10/2011 | Noriega et al. |
| 8,043,313 B2 | 10/2011 | Krolik et al. |
| 8,062,246 B2 | 11/2011 | Moutafis et al. |
| 8,062,257 B2 | 11/2011 | Moberg et al. |
| 8,065,096 B2 | 11/2011 | Moberg et al. |
| 8,066,677 B2 | 11/2011 | Lunn et al. |
| 8,070,694 B2 | 12/2011 | Galdonik et al. |
| 8,075,546 B2 | 12/2011 | Carlisle et al. |
| 8,092,483 B2 | 1/2012 | Galdonik et al. |
| 8,123,777 B2 | 2/2012 | Krolik et al. |
| 8,140,146 B2 | 3/2012 | Kim et al. |
| 8,142,458 B2 | 3/2012 | Shturman |
| 8,152,782 B2 | 4/2012 | Jang et al. |
| 8,152,951 B2 | 4/2012 | Zawacki et al. |
| 8,157,787 B2 | 4/2012 | Nash et al. |
| 8,162,877 B2 | 4/2012 | Bonnette et al. |
| 8,162,966 B2 | 4/2012 | Connor et al. |
| 8,177,739 B2 | 5/2012 | Cartledge et al. |
| 8,182,462 B2 | 5/2012 | Istoc et al. |
| 8,187,228 B2 | 5/2012 | Bikovsky |
| 8,187,229 B2 | 5/2012 | Weitzner et al. |
| 8,202,243 B2 | 6/2012 | Morgan |
| 8,209,060 B2 | 6/2012 | Ledford |
| 8,221,348 B2 | 7/2012 | Hackett et al. |
| 8,226,673 B2 | 7/2012 | Nash et al. |
| 8,246,573 B2 | 8/2012 | Ali et al. |
| 8,246,580 B2 | 8/2012 | Hopkins et al. |
| 8,257,298 B2 | 9/2012 | Hamboly |
| 8,257,343 B2 | 9/2012 | Chan et al. |
| 8,262,645 B2 | 9/2012 | Bagwell et al. |
| 8,267,893 B2 | 9/2012 | Moberg et al. |
| 8,287,485 B2 | 10/2012 | Kimura et al. |
| 8,291,337 B2 | 10/2012 | Gannin et al. |
| 8,292,841 B2 | 10/2012 | Gregersen |
| 8,308,745 B2 | 11/2012 | Seto et al. |
| 8,317,739 B2 | 11/2012 | Kueebler |
| 8,317,770 B2 | 11/2012 | Miesel et al. |
| 8,317,773 B2 | 11/2012 | Appling et al. |
| 8,317,786 B2 | 11/2012 | Dahla et al. |
| 8,323,239 B2 | 12/2012 | Bednarek et al. |
| 8,323,268 B2 | 12/2012 | Ring et al. |
| 8,337,175 B2 | 12/2012 | Dion et al. |
| 8,337,451 B2 | 12/2012 | Lareau et al. |
| 8,343,097 B2 | 1/2013 | Pile-Spellman et al. |
| 8,343,131 B2 | 1/2013 | Vinten-Johansen |
| 8,348,896 B2 | 1/2013 | Wagner |
| 8,353,858 B2 | 1/2013 | Kozak et al. |
| 8,353,860 B2 | 1/2013 | Boulais et al. |
| 8,357,138 B2 | 1/2013 | Pierpont et al. |
| 8,372,038 B2 | 2/2013 | Urich et al. |
| 8,394,078 B2 | 3/2013 | Torrance et al. |
| 8,398,579 B2 | 3/2013 | Morris et al. |
| 8,398,581 B2 | 3/2013 | Panotopoulos |
| 8,398,582 B2 | 3/2013 | Gordon et al. |
| 8,414,521 B2 | 4/2013 | Baker et al. |
| 8,414,522 B2 | 4/2013 | Kamen et al. |
| 8,414,943 B2 | 4/2013 | Wijngaarden et al. |
| 8,419,709 B2 | 4/2013 | Haddad et al. |
| 8,425,458 B2 | 4/2013 | Scopton |
| 8,430,837 B2 | 4/2013 | Jenson et al. |
| 8,430,845 B2 | 4/2013 | Wahr et al. |
| 8,430,861 B2 | 4/2013 | Schwartz et al. |
| 8,439,876 B2 | 5/2013 | Spohn et al. |
| 8,454,557 B1 | 6/2013 | Qi et al. |
| 8,465,456 B2 | 6/2013 | Stivland |
| 8,465,867 B2 | 6/2013 | Kim |
| 8,483,980 B2 | 7/2013 | Moberg et al. |
| 8,491,523 B2 | 7/2013 | Thor et al. |
| 8,500,697 B2 | 8/2013 | Kurth et al. |
| 8,506,537 B2 | 8/2013 | Torstensen et al. |
| 8,523,801 B2 | 9/2013 | Nash et al. |
| 8,529,498 B2 | 9/2013 | Moutafis et al. |
| 8,545,432 B2 | 10/2013 | Renati et al. |
| 8,545,514 B2 | 10/2013 | Ferrera |
| 8,562,555 B2 | 10/2013 | MacMahon et al. |
| 8,579,926 B2 | 11/2013 | Pintor et al. |
| 8,597,238 B2 | 12/2013 | Bonnette et al. |
| 8,608,699 B2 | 12/2013 | Blomquist |
| 8,613,618 B2 | 12/2013 | Brokx |
| 8,613,724 B2 | 12/2013 | Lanier et al. |
| 8,617,110 B2 | 12/2013 | Moberg et al. |
| 8,617,127 B2 | 12/2013 | Woolston et al. |
| 8,623,039 B2 | 1/2014 | Seto et al. |
| 8,628,549 B2 | 1/2014 | To et al. |
| 8,641,671 B2 | 2/2014 | Michaud et al. |
| 8,647,294 B2 | 2/2014 | Bonnette et al. |
| 8,652,086 B2 | 2/2014 | Gerg et al. |
| 8,657,777 B2 | 2/2014 | Kozak et al. |
| 8,657,785 B2 | 2/2014 | Torrance et al. |
| 8,663,259 B2 | 3/2014 | Levine et al. |
| 8,668,464 B2 | 3/2014 | Kensy et al. |
| 8,668,665 B2 | 3/2014 | Gerg et al. |
| 8,670,836 B2 | 3/2014 | Aeschlimann et al. |
| 8,672,876 B2 | 3/2014 | Jacobson et al. |
| 8,681,010 B2 | 3/2014 | Moberg et al. |
| 8,715,237 B2 | 5/2014 | Moberg et al. |
| 8,721,674 B2 | 5/2014 | Kusleika |
| 8,758,325 B2 | 6/2014 | Webster et al. |
| 8,758,364 B2 | 6/2014 | Eckhouse et al. |
| 8,783,151 B1 | 7/2014 | Janardhan et al. |
| 8,803,030 B1 | 8/2014 | Janardhan et al. |
| 8,814,892 B2 | 8/2014 | Galdonik et al. |
| 8,851,866 B2 | 10/2014 | Moutafis et al. |
| 8,852,219 B2 | 10/2014 | Wulfman et al. |
| 8,864,792 B2 | 10/2014 | Eckhouse et al. |
| 8,888,801 B2 | 11/2014 | To et al. |
| 8,900,179 B2 | 12/2014 | Jenson et al. |
| 8,900,214 B2 | 12/2014 | Nance et al. |
| 8,920,402 B2 | 12/2014 | Nash et al. |
| 8,932,320 B1 | 1/2015 | Janardhan et al. |
| 8,932,321 B1 | 1/2015 | Janardhan et al. |
| 8,936,447 B2 | 1/2015 | Abal |
| 8,945,030 B2 | 2/2015 | Weston |
| 8,962,561 B2 | 2/2015 | Shalgi et al. |
| 8,970,384 B2 | 3/2015 | Yodfat et al. |
| 8,974,418 B2 | 3/2015 | Bonnette et al. |
| 8,979,798 B2 | 3/2015 | Shener et al. |

(56) References Cited

U.S. PATENT DOCUMENTS

| | | |
|---|---|---|
| 8,986,241 B2 | 3/2015 | Evans et al. |
| 8,986,252 B2 | 3/2015 | Cummings et al. |
| 8,998,843 B2 | 4/2015 | Bonnette et al. |
| 9,005,237 B2 | 4/2015 | Eckhouse et al. |
| 9,011,114 B2 | 4/2015 | Farrell et al. |
| 9,017,294 B2 | 4/2015 | McGuckin et al. |
| 9,023,070 B2 | 5/2015 | Levine et al. |
| 9,024,768 B2 | 5/2015 | Mandro et al. |
| 9,033,925 B2 | 5/2015 | Moberg et al. |
| 9,034,008 B2 | 5/2015 | Eckhouse et al. |
| 9,042,938 B2 | 5/2015 | Nimbalker et al. |
| 9,078,691 B2 | 7/2015 | Morris et al. |
| 9,113,955 B2 | 8/2015 | Noriega et al. |
| 9,119,941 B2 | 9/2015 | Rollins et al. |
| 9,119,942 B1 | 9/2015 | Rollins et al. |
| 9,198,679 B2 | 12/2015 | To et al. |
| 9,238,122 B2 | 1/2016 | Malhi et al. |
| 9,248,221 B2 | 2/2016 | Look et al. |
| 9,254,144 B2 | 2/2016 | Nguyen et al. |
| 9,278,189 B2 | 3/2016 | Corbett |
| 9,282,992 B2 | 3/2016 | Levine et al. |
| 9,283,040 B2 | 3/2016 | Hendrick et al. |
| 9,308,016 B2 | 4/2016 | Escudero et al. |
| 9,314,263 B2 | 4/2016 | Escudero et al. |
| 9,332,999 B2 | 5/2016 | Ray et al. |
| 9,333,007 B2 | 5/2016 | Escudero et al. |
| 9,358,035 B2 | 6/2016 | Kojima |
| 9,402,938 B2 | 8/2016 | Aklog et al. |
| 9,433,427 B2 | 9/2016 | Look et al. |
| 9,456,872 B2 | 10/2016 | Hendrick et al. |
| 9,474,543 B2 | 10/2016 | McGuckin et al. |
| 9,492,192 B2 | 11/2016 | To et al. |
| 9,492,193 B2 | 11/2016 | To et al. |
| 9,510,854 B2 | 12/2016 | Mallaby |
| 9,586,023 B2 | 3/2017 | Bonnette et al. |
| 9,592,073 B2 | 3/2017 | Kojima et al. |
| 9,597,480 B2 | 3/2017 | Purdy et al. |
| 9,693,789 B2 | 7/2017 | Garrison et al. |
| 9,700,346 B2 | 7/2017 | Levine et al. |
| 9,770,551 B1 | 9/2017 | Faden |
| 9,782,195 B2 | 10/2017 | MacTaggart et al. |
| 9,795,406 B2 | 10/2017 | Levine et al. |
| 9,808,266 B2 | 11/2017 | Ray et al. |
| 9,827,404 B2 | 11/2017 | Nance et al. |
| 9,833,257 B2 | 12/2017 | Bonnette et al. |
| 9,883,877 B2 | 2/2018 | Look et al. |
| 10,238,853 B2 | 3/2019 | Kume et al. |
| 10,314,608 B2 | 6/2019 | Jenson et al. |
| 10,383,983 B2 | 8/2019 | Aklog et al. |
| 10,390,926 B2 | 8/2019 | Janardhan et al. |
| 10,426,885 B2 | 10/2019 | Criado et al. |
| 10,499,944 B2 | 12/2019 | Mallaby |
| 10,531,883 B1 | 1/2020 | DeVille et al. |
| 10,702,292 B2 | 7/2020 | Look et al. |
| 10,716,880 B2 | 7/2020 | Culbert et al. |
| 2001/0004700 A1 | 6/2001 | Honeycutt et al. |
| 2001/0051811 A1 | 12/2001 | Bonnette et al. |
| 2002/0016564 A1 | 2/2002 | Courtney et al. |
| 2002/0029052 A1 | 3/2002 | Evans et al. |
| 2002/0058904 A1 | 5/2002 | Boock et al. |
| 2002/0068895 A1 | 6/2002 | Beck |
| 2002/0133114 A1 | 9/2002 | Itoh et al. |
| 2002/0138095 A1 | 9/2002 | Mazzocchi et al. |
| 2002/0165575 A1 | 11/2002 | Saleh |
| 2002/0173819 A1 | 11/2002 | Leeflang et al. |
| 2002/0176788 A1 | 11/2002 | Moutafis et al. |
| 2002/0177789 A1 | 11/2002 | Ferry et al. |
| 2003/0032918 A1 | 2/2003 | Quinn |
| 2003/0040694 A1 | 2/2003 | Dorros et al. |
| 2003/0055404 A1 | 3/2003 | Moutafis |
| 2003/0069549 A1 | 4/2003 | MacMahon et al. |
| 2003/0083681 A1 | 5/2003 | Moutafis et al. |
| 2003/0088187 A1 | 5/2003 | Saadat et al. |
| 2003/0088209 A1 | 5/2003 | Chiu et al. |
| 2003/0139751 A1 | 7/2003 | Evans et al. |
| 2003/0144688 A1 | 7/2003 | Brady et al. |
| 2003/0216760 A1 | 11/2003 | Welch et al. |
| 2003/0220556 A1 | 11/2003 | Porat et al. |
| 2003/0236533 A1 | 12/2003 | Wilson et al. |
| 2004/0030281 A1 | 2/2004 | Goble et al. |
| 2004/0049149 A1 | 3/2004 | Drasler et al. |
| 2004/0049225 A1 | 3/2004 | Denison |
| 2004/0054322 A1 | 3/2004 | Vargas |
| 2004/0082915 A1 | 4/2004 | Kadan |
| 2004/0087988 A1 | 5/2004 | Heitzmann et al. |
| 2004/0097829 A1 | 5/2004 | McRury et al. |
| 2004/0143225 A1 | 7/2004 | Callan et al. |
| 2004/0147871 A1 | 7/2004 | Burnett |
| 2004/0153109 A1 | 8/2004 | Tiedtke et al. |
| 2004/0158136 A1 | 8/2004 | Gough et al. |
| 2004/0167463 A1 | 8/2004 | Zawacki et al. |
| 2004/0193046 A1 | 9/2004 | Nash et al. |
| 2004/0199201 A1 | 10/2004 | Kellet et al. |
| 2004/0215222 A1 | 10/2004 | Krivoruchko |
| 2004/0236214 A1 | 11/2004 | Opie et al. |
| 2004/0243157 A1 | 12/2004 | Connor et al. |
| 2005/0004594 A1 | 1/2005 | Nool et al. |
| 2005/0043682 A1 | 2/2005 | Kucklick et al. |
| 2005/0049547 A1 | 3/2005 | Anspach et al. |
| 2005/0065426 A1 | 3/2005 | Porat et al. |
| 2005/0085769 A1 | 4/2005 | MacMahon et al. |
| 2005/0102165 A1 | 5/2005 | Oshita et al. |
| 2005/0159716 A1 | 7/2005 | Kobayashi et al. |
| 2005/0196748 A1 | 9/2005 | Ericson |
| 2005/0238503 A1 | 10/2005 | Rush et al. |
| 2005/0240116 A1 | 10/2005 | Saadat et al. |
| 2005/0240120 A1 | 10/2005 | Modesitt |
| 2005/0240146 A1 | 10/2005 | Nash et al. |
| 2005/0244521 A1 | 11/2005 | Strickland et al. |
| 2005/0277851 A1 | 12/2005 | Whittaker et al. |
| 2005/0283150 A1 | 12/2005 | Moutafis et al. |
| 2006/0009785 A1 | 1/2006 | Maitland et al. |
| 2006/0041245 A1 | 2/2006 | Ferry et al. |
| 2006/0058836 A1 | 3/2006 | Bose et al. |
| 2006/0063973 A1 | 3/2006 | Makower et al. |
| 2006/0064051 A1 | 3/2006 | Gross |
| 2006/0064123 A1 | 3/2006 | Bonnette et al. |
| 2006/0074442 A1 | 4/2006 | Noriega et al. |
| 2006/0093989 A1 | 5/2006 | Hahn et al. |
| 2006/0142630 A1 | 6/2006 | Meretei |
| 2006/0149191 A1 | 7/2006 | DiFiore |
| 2006/0184186 A1 | 8/2006 | Noone |
| 2006/0212055 A1 | 9/2006 | Karabey et al. |
| 2006/0229550 A1* | 10/2006 | Staid ............... A61B 17/3203 604/27 |
| 2006/0229587 A1 | 10/2006 | Beyar et al. |
| 2006/0264808 A1 | 11/2006 | Staid et al. |
| 2006/0282150 A1 | 12/2006 | Olson et al. |
| 2007/0016105 A1 | 1/2007 | Mamourian |
| 2007/0060879 A1 | 3/2007 | Weitzner et al. |
| 2007/0073233 A1 | 3/2007 | Thor et al. |
| 2007/0073268 A1 | 3/2007 | Goble et al. |
| 2007/0078438 A1 | 4/2007 | Okada |
| 2007/0118165 A1 | 5/2007 | DeMello et al. |
| 2007/0135812 A1 | 6/2007 | Sartor |
| 2007/0167804 A1 | 7/2007 | Park et al. |
| 2007/0197956 A1 | 8/2007 | Le et al. |
| 2007/0197963 A1 | 8/2007 | Griffiths et al. |
| 2007/0219467 A1 | 9/2007 | Clark et al. |
| 2007/0225615 A1 | 9/2007 | Chechelski et al. |
| 2007/0225739 A1 | 9/2007 | Pintor et al. |
| 2007/0239182 A1 | 10/2007 | Glines et al. |
| 2007/0249990 A1 | 10/2007 | Cosmescu |
| 2007/0270755 A1 | 11/2007 | Von Oepen et al. |
| 2007/0299306 A1 | 12/2007 | Parasher et al. |
| 2008/0009784 A1 | 1/2008 | Leedle et al. |
| 2008/0091061 A1 | 4/2008 | Kumar et al. |
| 2008/0097339 A1 | 4/2008 | Ranchod et al. |
| 2008/0097465 A1 | 4/2008 | Rollins et al. |
| 2008/0097563 A1 | 4/2008 | Petrie et al. |
| 2008/0108960 A1 | 5/2008 | Shapland et al. |
| 2008/0119824 A1 | 5/2008 | Weitzner et al. |
| 2008/0125698 A1 | 5/2008 | Gerg et al. |
| 2008/0125798 A1 | 5/2008 | Osborne et al. |

(56) References Cited

U.S. PATENT DOCUMENTS

| | | |
|---|---|---|
| 2008/0195058 A1 | 8/2008 | Moutafis et al. |
| 2008/0195139 A1 | 8/2008 | Donald et al. |
| 2008/0243054 A1 | 10/2008 | Mollstam et al. |
| 2008/0243153 A1 | 10/2008 | Nguyen et al. |
| 2008/0249501 A1 | 10/2008 | Yamasaki |
| 2008/0255539 A1 | 10/2008 | Booth |
| 2008/0255596 A1 | 10/2008 | Jenson et al. |
| 2008/0294008 A1 | 11/2008 | Toyama |
| 2008/0294181 A1 | 11/2008 | Wensel et al. |
| 2008/0306465 A1 | 12/2008 | Bailey et al. |
| 2008/0319376 A1 | 12/2008 | Wilcox et al. |
| 2009/0018566 A1 | 1/2009 | Escudero et al. |
| 2009/0048607 A1 | 2/2009 | Rockley |
| 2009/0054825 A1 | 2/2009 | Melsheimer et al. |
| 2009/0082722 A1 | 3/2009 | Munger et al. |
| 2009/0105645 A1 | 4/2009 | Kidd et al. |
| 2009/0105690 A1 | 4/2009 | Schaeffer et al. |
| 2009/0157057 A1 | 6/2009 | Ferren et al. |
| 2009/0264940 A1 | 10/2009 | Beale et al. |
| 2009/0292212 A1 | 11/2009 | Ferren et al. |
| 2009/0306476 A1 | 12/2009 | Banik et al. |
| 2009/0306692 A1 | 12/2009 | Barrington et al. |
| 2010/0010524 A1 | 1/2010 | Barrington et al. |
| 2010/0030134 A1 | 2/2010 | Fitzgerald et al. |
| 2010/0030186 A1 | 2/2010 | Stivland |
| 2010/0094201 A1 | 4/2010 | Mallaby |
| 2010/0145302 A1 | 6/2010 | Cull et al. |
| 2010/0174233 A1 | 7/2010 | Kuban et al. |
| 2010/0191178 A1 | 7/2010 | Ross et al. |
| 2010/0204613 A1 | 8/2010 | Rollins et al. |
| 2010/0204672 A1 | 8/2010 | Lockhart et al. |
| 2010/0217275 A1 | 8/2010 | Carmeli et al. |
| 2010/0217276 A1 | 8/2010 | Garrison et al. |
| 2010/0228273 A1 | 9/2010 | Staid et al. |
| 2010/0268236 A1 | 10/2010 | Moutafis et al. |
| 2010/0274191 A1 | 10/2010 | Ting |
| 2010/0280534 A1 | 11/2010 | Sher |
| 2011/0034986 A1 | 2/2011 | Chou et al. |
| 2011/0091331 A1 | 4/2011 | Moutafis et al. |
| 2011/0092892 A1 | 4/2011 | Nitsan et al. |
| 2011/0106019 A1 | 5/2011 | Bagwell et al. |
| 2011/0152920 A1 | 6/2011 | Eckhouse et al. |
| 2011/0160683 A1 | 6/2011 | Pinotti et al. |
| 2011/0282426 A1 | 11/2011 | Mitra et al. |
| 2012/0059340 A1 | 3/2012 | Larsson |
| 2012/0059354 A1 | 3/2012 | Zarate |
| 2012/0065656 A1 | 3/2012 | Karwei |
| 2012/0065660 A1 | 3/2012 | Ferrera et al. |
| 2012/0071907 A1 | 3/2012 | Pintor et al. |
| 2012/0078080 A1 | 3/2012 | Foley et al. |
| 2012/0123509 A1 | 5/2012 | Merrill et al. |
| 2012/0130415 A1 | 5/2012 | Tal et al. |
| 2012/0165756 A1 | 6/2012 | Root et al. |
| 2012/0239008 A1 | 9/2012 | Fojtik |
| 2012/0239064 A1 | 9/2012 | Cartier et al. |
| 2012/0239066 A1 | 9/2012 | Levine et al. |
| 2012/0259265 A1 | 10/2012 | Salehi et al. |
| 2012/0277665 A1 | 11/2012 | Tachoire et al. |
| 2012/0289910 A1 | 11/2012 | Shtul et al. |
| 2012/0291811 A1 | 11/2012 | Dabney et al. |
| 2012/0330196 A1 | 12/2012 | Nita |
| 2013/0085381 A1 | 4/2013 | Comerota et al. |
| 2013/0184734 A1 | 7/2013 | Morris et al. |
| 2013/0190701 A1 | 7/2013 | Kirn |
| 2013/0218186 A1 | 8/2013 | Dubois et al. |
| 2013/0245543 A1 | 9/2013 | Gerg et al. |
| 2013/0267891 A1 | 10/2013 | Malhi et al. |
| 2013/0281788 A1 | 10/2013 | Garrison |
| 2013/0310809 A1 | 11/2013 | Armstrong |
| 2013/0310845 A1 | 11/2013 | Thor et al. |
| 2013/0331776 A1 | 12/2013 | Klein et al. |
| 2014/0005699 A1 | 1/2014 | Bonnette et al. |
| 2014/0058361 A1 | 2/2014 | Gordon |
| 2014/0142594 A1 | 5/2014 | Fojtik |
| 2014/0147246 A1 | 5/2014 | Chappel et al. |
| 2014/0148830 A1 | 5/2014 | Bowman |
| 2014/0155931 A1 | 6/2014 | Bose et al. |
| 2014/0228569 A1 | 8/2014 | Okumura et al. |
| 2014/0228869 A1 | 8/2014 | Bonnette et al. |
| 2014/0276920 A1 | 9/2014 | Hendrick et al. |
| 2014/0309589 A1 | 10/2014 | Momose et al. |
| 2014/0323906 A1 | 10/2014 | Peatfield et al. |
| 2014/0037895 A1 | 12/2014 | Dye |
| 2014/0360494 A1 | 12/2014 | Herskovic |
| 2014/0378951 A1 | 12/2014 | Dye |
| 2015/0025446 A1 | 1/2015 | Jacobson et al. |
| 2015/0032138 A1 | 1/2015 | Jenson et al. |
| 2015/0094673 A1 | 4/2015 | Pratt et al. |
| 2015/0094748 A1 | 4/2015 | Nash et al. |
| 2015/0142030 A1 | 5/2015 | MacTaggart et al. |
| 2015/0257724 A1 | 9/2015 | Lautenschläger |
| 2015/0305765 A1 | 10/2015 | Fojtik et al. |
| 2015/0327875 A1 | 11/2015 | Look et al. |
| 2015/0374391 A1 | 12/2015 | Quick et al. |
| 2016/0051323 A1 | 2/2016 | Stigall et al. |
| 2016/0058614 A1 | 3/2016 | Ross et al. |
| 2016/0143721 A1 | 5/2016 | Rosenbluth et al. |
| 2016/0220741 A1 | 8/2016 | Garrison et al. |
| 2017/0065396 A1 | 3/2017 | Look et al. |
| 2017/0079672 A1 | 3/2017 | Quick |
| 2017/0105745 A1 | 4/2017 | Rosenbluth et al. |
| 2017/0172603 A1 | 6/2017 | Bonnette et al. |
| 2017/0181760 A1 | 6/2017 | Look et al. |
| 2017/0265885 A1 | 9/2017 | Bonnette et al. |
| 2017/0281204 A1 | 10/2017 | Garrison et al. |
| 2017/0290598 A1 | 10/2017 | Culbert et al. |
| 2018/0207397 A1 | 7/2018 | Look et al. |
| 2018/0214172 A1 | 8/2018 | Donnelly et al. |
| 2018/0338770 A1 | 11/2018 | Mogi et al. |
| 2020/0345904 A1 | 11/2020 | Casey et al. |
| 2020/0367917 A1 | 11/2020 | Teigen et al. |

FOREIGN PATENT DOCUMENTS

| | | |
|---|---|---|
| CN | 201603160 U | 10/2010 |
| CN | 103767760 A | 5/2014 |
| DE | 3715418 A1 | 11/1987 |
| DE | 4018736 A1 | 1/1992 |
| EP | 0709110 A1 | 5/1996 |
| EP | 0726466 A1 | 8/1996 |
| EP | 0806213 A1 | 11/1997 |
| EP | 1092396 A2 | 4/2001 |
| EP | 1488748 A1 | 12/2004 |
| EP | 2301450 A1 | 3/2011 |
| EP | 2859902 A1 | 4/2015 |
| EP | 2131759 B1 | 10/2017 |
| JP | 6125915 A | 5/1994 |
| JP | 06-205784 A | 7/1994 |
| JP | 6205785 A | 7/1994 |
| JP | 7299078 A | 11/1995 |
| JP | 2001161700 A | 6/2001 |
| JP | 2003-010194 A | 1/2003 |
| JP | 20030101194 A | 1/2003 |
| JP | 2003514632 A | 4/2003 |
| JP | 2003-260127 A | 9/2003 |
| JP | 2003290236 A | 10/2003 |
| JP | 2004514466 A | 5/2004 |
| JP | 2007160109 A | 6/2007 |
| JP | 2009-039216 A | 2/2009 |
| JP | 2013-154171 A | 8/2013 |
| JP | 2013180156 A | 12/2013 |
| WO | 90/05493 A1 | 5/1990 |
| WO | 9601079 A1 | 1/1996 |
| WO | 96/35469 A1 | 11/1996 |
| WO | 99/01079 A1 | 1/1999 |
| WO | 99/18850 A1 | 4/1999 |
| WO | 00/69348 A1 | 11/2000 |
| WO | 01/37916 A1 | 5/2001 |
| WO | 02/19928 A2 | 3/2002 |
| WO | 0226289 A1 | 4/2002 |
| WO | 2004100772 A2 | 11/2004 |
| WO | 2005/004968 A1 | 1/2005 |
| WO | 2006/081238 A2 | 8/2006 |
| WO | 2007/087404 A2 | 8/2007 |

(56) References Cited

FOREIGN PATENT DOCUMENTS

| WO | 2007/143633 A2 | 12/2007 |
| --- | --- | --- |
| WO | 2008/097993 A2 | 8/2008 |
| WO | 2008/121481 A1 | 10/2008 |
| WO | 2010/023617 A1 | 3/2010 |
| WO | 2010023671 A2 | 3/2010 |
| WO | 2015/179329 A1 | 11/2015 |
| WO | 2016/126974 A1 | 8/2016 |
| WO | 2017/112922 A1 | 6/2017 |
| WO | 2018/215840 A1 | 11/2018 |

OTHER PUBLICATIONS

"Angiojet Ultra Power Pulse Kit Information for Use", Medrad, Inc., downloaded from internet Jan. 23, 2017.

Comparison of Dimensions and Aspiration Rate of the Pronto V3, Pronto LP, Export XT, Export AP, Fetch, Xtract, Diver C.E, and QuickCat Catheter, Vascular Solutions, Inc., downloaded from internet Oct. 22, 2014.

Dalal, J., Sahoo, P., Dhall, A., Kapoor, R., Krishnamurthy, A., Shetty, S., Trivedi, S., Kahali, D., Shah, B., Chockalingam, K., Abdullakutty, J., Shetty, P., Chopra, A., Ray, R., Desai, D., Pachiyappan, Ratnaparkhi, G. , Sharma, M., Sambasivam, K. "Role of thrombysis in reperfusion therapy for management of AMI: Indian scenario," Indian Heart Journal, 2013, pp. 566-585, vol. 63, Cardiological Society of India, Bombay, India.

Franetzki, M., "Confusion in the Terminology of Insulin Devices", Diabetes Care, Jan.-Feb. 1982, pp. 74-75, vol. 5, No. 1, American Diabetes Association, Alexandria, USA.

Frolich, G., Meier, P., White, S., Yellon, D., Hausenloy, D., "Myocardial reperfusion injury: looking beyond primary PCI", European Heart Journal Jun. 2013, pp. 1714-1722, vol. 34, No. 23, Elsevier, Amsterdam, The Netherlands.

Gousios, A, Sheam, M, "Effect of Intravenous Heparin on Human Blood Viscosity", Circulation, Dec. 1959, pp. 1063-1066, vol. 20, American Heart Association, Dallas, USA.

Harvard Health; Normal Body Temperature: Rethinking the normal human body temperature; p. 1; published Apr. 1, 2006; http://www.health.harvard.edu/press.sub.—releases/normal.sub.—body.sub.—temperature.

Infusion Liquid Flow Sensors—Safe, Precise and Reliable, Sensirion, downloaded from Internet Apr. 3, 2015.

Irsigler, K, Kritz, H., Hagmuller, G., Franezki, M., Prestele, K, Thurow, H., Geisen, K., "Long-term Continuous Intraperitoneal Insulin Infusion with an Implanted Remote-Controlled Insulin Infusion Device", Diabetes, Dec. 1981, pp. 1072-1075, vol. 30, No. 12, American Diabetes Association, New York, USA.

Kritz, H., Hagmuller, G, Lovett, R., Irsigler, K., "Implanted Constant Basal Rate Insulin Infusion Devices for Type 1 (Insulin-Dependent) Diabetic Patients", Diabetologia, Aug. 1983, pp. 78-81, vol. 25, No. 2, Springer-Veriag, Berlin, Germany.

Lipinski, M., Lee, R., Gaglia, M., Torguson, R., Garcia-Garcia, H., Pichard, A., Satler, L., Waksman, R. "Comparison of heparin, bivalirudin, and different glycoprotein llb/llla inhibitor regimens for anticoagulation during percutaneous coronary intervention: A network meta-analysis," Cardiovascular Revascularization Medicine, 2016, pp. 535-545, vol. 17, Elsevier, New York, USA.

Makes even the most difficult intervention a Fast and Smooth Run. GuideLiner brochure. Vascular Solutions,. Inc., downloaded from internet Apr. 9, 2015.

Metzler, L., "Miniature Sensor Combines with Micropump to Control Drug Delivery", Medical Design Technology, Mar. 2017, pp. 22-23, MDTmag.com, Advantage Business Media, Rockaway, USA.

Parikh, A., Ali, F., "Novel Use of GuideLiner Catheter to Perform Aspiration Thrombectomy in a Saphenous Vein Graft" Cath Lab Digest, Oct. 2013, downloaded from internet Oct. 22, 2014.

Pechlaner, C., Knapp, E., Wiedermann, C. "Hypersensitivity reactions associated with recombinant tissue-type plasminogen activator and urokinase," Blood Coagulation and Fibrinolysis, 2001, pp. 491-494, vol. 12, Lippincott Williams & Wilkins, Hagerstown, USA.

Prasad, A., Stone, G., Holmes, D., Gersh, B., Peperfusion Injury, Microvascular Dysfunction, and Carioprotection: The "Dark Side" of Reperfusion, Circulation, Nov. 24, 2009, pp. 2105-2112, vol. 120, American Heart Association, Dallas, USA.

Principles and Practice of Pharmacology for Anaesthetists, ed. Calvey, T., Williams, N., 2008, pp. 324-327, 5th Edition, Blackwell Publishing, Malden, USA.

Puddu, P., lanetta, L., Placanica, A., Cuturello, D., Schiariti, M., Manfrini, O., "The role of Glycoprotein llb/llla inhibitors in acute coronary syndromes and the interference with anemia," International Journal of Cardiology, 2016, pp. 1091-1096, vol. 222, Elsevier, Amsterdam, The Netherlands.

Rodriquez, R., Conde-Green, A., "Quantification of Negative Pressures Generated by Syringes of Different Calibers Used for Liposuction", Plastic & Reconstructive Surgery, Aug. 2012; pp. 383e-384e, vol. 130, No. 2, Lippicott Williams & Wilkins, Philadelphia, USA.

Saudek, C., Selam, J-L, Pitt, H., Waxman, K., Rubio, M., Jeandidier, N., Turner, D., Fischell, R., Charles, M., "A Preliminary trial of the Programmable Implantable Medication System for Insulin Delivery", The New England Journal of Medicine, Aug. 31, 1989, pp. 574-579, vol. 321, No. 9, Massachusetts Medical Society, Boston, USA.

Selam, J-L, "Development of Implantable Insulin Pumps: Long is the Road", Diabetic Medicine, Nov. 1988, pp. 724-733, vol. 5, No. 8, Wiley, Chichester, UK.

Stys, A., Stys, T., Rajpurohit, N., Khan, M. "A Novel Application of GuideLiner Catheter for Thrombectomy in Acute Myocardial Infarction: A Case Series", Journal of Invasive cardiology, Nov. 2013, pp. 620-624, vol. 25, No. 11, King of Prussia, USA.

Van De Werf, F, "The ideal fibrinolytic: can drug design improve clinical results?" European Heart Journal, 1999, pp. 1452-1458, vol. 20, Elsevier, Amsterdam, The Netherlands.

Warmerdam, P., Vanderlick, K., Vandervoort, P., de Smedt, H., Plaisance, S., De Maeyer, M., Collen, D. "Saphylokinase-Specific-Cell-Mediated Immunity in Humans," The Journal of Immunology, 2002, pp. 155-161, vol. 168, Williams & Wilkins Co., Baltimore, USA.

Micossi, et al., "One-Year Trial of a Remote-Controlled Implantable Insulin Infusion System in Type I Diabetic Patients", The Lancet, Oct. 15, 1998, pp. 866-869, vol. 2, No. 8616, Little, Brown & Co, Boston, USA.

Extended European Search Report dated Aug. 31, 2015, in EP App. No. 16843162.5 filed Sep. 3, 2016 (10 pages).

PCT International Search Report and Written Opinion for PCT/US2016/050302, Applicant: Vesatek, LLC, Forms PCT.ISA/220, 210, and 237 dated Nov. 29, 2016 (10 pages).

\* cited by examiner

THROMBECTOMY APPARATUS AND METHOD

RELATED APPLICATIONS

This application is a continuation of U.S. application Ser. No. 15/497,357, filed Apr. 26, 2017, which is a continuation of U.S. application Ser. No. 14/513,579, filed Oct. 14, 2014, now U.S. Pat. No. 9,662,137, which is a continuation of U.S. application Ser. No. 12/040,179 filed Feb. 29, 2008, now U.S. Pat. No. 8,900,179, which is a continuation of U.S. application Ser. No. 12/026,317, filed Feb. 5, 2008, now U.S. Pat. No. 8,430,837, which claims priority to U.S. Provisional Application No. 60/888,265 filed Feb. 5, 2007.

TECHNICAL FIELD

The present invention pertains generally to medical devices and methods of their use. More particularly, the present invention pertains to thrombectomy devices and methods of their use.

BACKGROUND

A variety of methods have been developed to remove thrombi and other unwanted material from a patient's vasculature. Examples include thrombolytic medications and mechanical devices such as fluid jets, ultrasound, laser, thermal, suction, balloons, rotating burrs, cutters, baskets, and wires. Thrombolytic medications are simpler to administer and have advantages in reaching any desired vessel, but disadvantages in slower action, monitoring requirements, bleeding complications, high cost, inability to remove harder or more organized thrombi, and travel to other vessels besides the target vessel. Mechanical devices are often faster and are specific to the target vessel, but have disadvantages in being larger size, difficulty in reaching a target vessel, local injury to the vessel wall, mechanical plugging, complicated and time-consuming setup, complicated operation requiring operator training and skill, and high cost; the effectiveness on harder or more organized thrombi varies, with the more effective devices being more invasive, more dangerous, or more expensive.

There are many situations in which it is desirable to remove thrombus or blood clots from the body, particularly in large blood vessels, heart chambers, or in extravascular spaces which could fill with blood during hemorrhage such as retroperitoneal bleeding, or other spaces such as cerebrospinal fluid spaces, hollow body organs, and so forth.

Existing thrombectomy devices, including fluid jet thrombectomy devices, have difficulty in treating large thrombi and in efficiently and effectively removing thrombus from large diameter vessels. A fluid Jet catheter may obtain some mixing and work at some distance, but doing so safely and capturing all the thrombus for removal is problematic. A variety of thrombus removal catheters can be utilized in smaller vessels such as coronary or leg arteries, and so forth.

Thus, a need remains for improved thrombus removal capability particularly for large vessels, including peripheral or central veins, pulmonary arteries and branches, chambers of the heart, larger arteries, and vascular prostheses.

SUMMARY

The invention pertains generally to devices for removing thrombi and other unwanted materials from within vessels such as relatively large arteries and veins. In an illustrative but non-limiting example, a thrombectomy system may include an elongate shaft that defines a high pressure lumen and a low pressure lumen. The high pressure lumen may terminate near an end of the low pressure lumen. An expandable capture basket may be disposed near the end of the low pressure lumen. In some applications, the thrombectomy system may function without a capture basket.

In another illustrative but non-limiting example, a thrombectomy apparatus may include an elongate shaft, an evacuation lumen extending within the elongate shaft and a high pressure lumen extending within the elongate shaft. A capture apparatus may be disposed within a wire lumen that extends within the elongate shaft such that the capture apparatus extends distally from the wire lumen.

In another illustrative but non-limiting example, an apparatus may include a first catheter shaft segment and a second catheter shaft segment. The first catheter shaft segment may have a suction lumen and a high pressure lumen. The second catheter shaft segment may have a wire lumen and a capture apparatus that is disposed at least partially within the wire lumen.

In another illustrative but non-limiting example, thrombi may be removed from within a vessel by using a high pressure jet as an ejector/aspiration device to pull the thrombi within the suction lumen. The captured thrombi may be disrupted by the high pressure jet and the disrupted thrombi may be suctioned out of the vessel. In such apparatus, the high pressure jet may be located near the distal opening of the distal tip. In some embodiments, the high pressure jet may exit a high pressure lumen at an angle which generally parallels a proximal slope associated with the distal opening or at an angle which is somewhat more inclined toward an axial orientation.

In another illustrative but non-limiting example, thrombi may be removed from within a vessel by capturing the thrombi within a capture apparatus. The captured thrombi may be disrupted with a high pressure jet and then the disrupted thrombi may be suctioned out of the vessel.

In another illustrative but non-limiting example, thrombi may be removed by providing a thrombectomy apparatus similar to that described above. The thrombectomy apparatus may be advanced to a desired location within a patient's vasculature. The expandable capture basket may be expanded, and thrombi may be captured therein. A high pressure fluid source may be provided via the high pressure lumen in order to break apart the captured thrombi. Suction may be applied to the low pressure lumen in order to evacuate the broken apart thrombi.

The above summary of some embodiments is not intended to describe each disclosed embodiment or every implementation of the present invention. The Figures and Detailed Description that follow more particularly exemplify these embodiments.

BRIEF DESCRIPTION OF THE FIGURES

The invention may be more completely understood in consideration of the following detailed description of various embodiments of the invention in connection with the accompanying drawings, in which.

Figure 1:
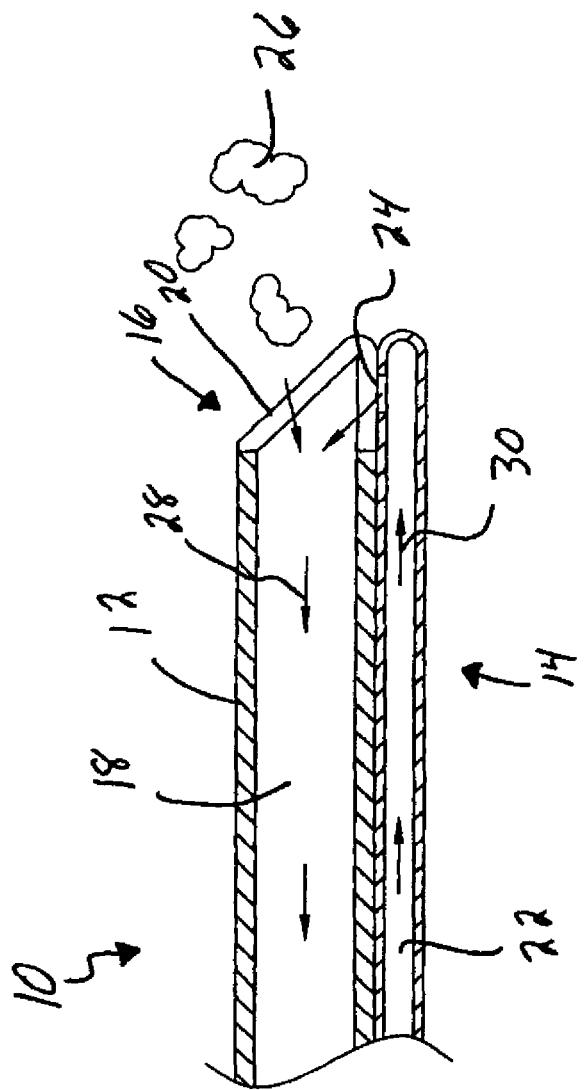
FIG. 1 is a diagrammatic view of a portion of a thrombectomy apparatus in accordance with an embodiment of the invention.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention.

DETAILED DESCRIPTION

For the following defined terms, these definitions shall be applied, unless a different definition is given in the claims or elsewhere in this specification.

All numeric values are herein assumed to be modified by the term "about," whether or not explicitly indicated. The term "about" generally refers to a range of numbers that one of skill in the art would consider equivalent to the recited value (i.e., having the same function or result). In many instances, the terms "about" may include numbers that are rounded to the nearest significant figure.

The recitation of numerical ranges by endpoints includes all numbers within that range (e.g. 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

The following detailed description should be read with reference to the drawings in which similar elements in different drawings are numbered the same. The drawings, which are not necessarily to scale, depict illustrative embodiments and are not intended to limit the scope of the invention.

The invention pertains generally to a thrombectomy apparatus that includes a low pressure or evacuation lumen, a high pressure lumen and an expandable capture basket. In some cases, a thrombectomy apparatus may be provided within an external sheath for storage, transportation and/or delivery.

Merely for clarity, some Figures show only certain elements of the invention while not showing certain other elements. It will be understood that these elements may be combined as desired in practicing the invention.

FIG. 1 is a schematic cross-sectional view of a portion of a thrombectomy catheter 10. The thrombectomy catheter 10 includes an elongate shaft 12 that has a distal region 14 defining a distal end 16. In the illustrated embodiment, a low pressure or evacuation lumen 18 extends through the distal region 12 and may, as shown, extend to the distal end 14. The evacuation lumen 18 may terminate at a distal opening 20. A high pressure lumen 22 may extend through the distal region 14. The high pressure lumen 22 may terminate at a distal opening 24.

In some instances, as illustrated, the high pressure lumen 22 may extend at least substantially parallel with the evacuation lumen 18. In some cases, the high pressure lumen 22 may be formed by a tubular member extending within the evacuation lumen 18. While not expressly shown in this Figure, it will be recognized that the elongate shaft 12 may include one or more additional lumens such as a capture basket lumen, a guidewire lumen, and the like.

In FIG. 1, the thrombectomy catheter 12 may be considered as being disposed within a patient's vasculature or other desired lumen or void that may contain thrombi or other undesirable material, although the environment is not expressly shown. Thrombi 26 are generically shown disposed just distal of the distal end 16 of the elongate shaft 12. Thrombi 26 may be drawn towards and into the evacuation lumen 18 by applying a low pressure source to a proximal end (not illustrated) of the evacuation lumen 18. A low pressure source may provide suction, such as a vacuum source. The low pressure within the evacuation lumen 18 may be generically represented by arrows 28. These arrows 28 also indicate the direction in which the thrombi 26 will travel through the evacuation lumen 18.

In some cases, if desired, a high pressure fluid source may be placed in fluid communication with the high pressure lumen 22. A suitable fluid such as saline or another therapeutically acceptable fluid may travel in a direction indicated by arrows 30. In some instances, the high pressure fluid may exit the high pressure lumen 22 through the distal opening 24. In some cases, the distal opening 24 may be a jet orifice that causes the high pressure fluid to exit therefrom at a high rate of speed. The high pressure fluid may, therefore, impact the thrombi 26 and at least partially break the thrombi 26 into smaller pieces that may better fit through the evacuation lumen 18 without clogging the evacuation lumen 18.

In some cases, as illustrated, the distal opening 24 of the high pressure lumen 22 may be positioned relative to the distal opening 20 of the evacuation lumen 18 such that the high pressure fluid creates a jet that extends at least partially across the distal opening 20. As will be discussed with respect to subsequent Figures, the distal opening 24 may have a variety of different locations relative to the distal opening 20 of the evacuation lumen 18.

The elongate shaft 12 may be formed of any suitable materials. In some cases, the elongate shaft 12 may be formed of one or more suitable polymeric materials. Examples of suitable polymers include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane, polypropylene (PP), polyvinylchloride (PVC), polyether-ester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), Marlex high-density polyethylene, Marlex low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro(propyl vinyl ether) (PFA), ethylene vinyl alcohol, polyolefin, polystyrene, epoxy, polyvinylidene chloride (PVdC), polycarbonates, ionomers, biocompatible polymers, other suitable materials, or mixtures, combinations, copolymers thereof, polymer/metal composites, and the like.

In some cases, the evacuation lumen 18 and the high pressure lumen 22 may be formed as parallel lumens within a single catheter shaft. In some cases, the evacuation lumen 18 may be formed within a catheter shaft or as a separate elongate tubular member while the high pressure lumen 22 may be formed as an elongate tube provided at least partially on the exterior of the catheter shaft or elongate tubular member forming the evacuation lumen 18.

Figure 2:
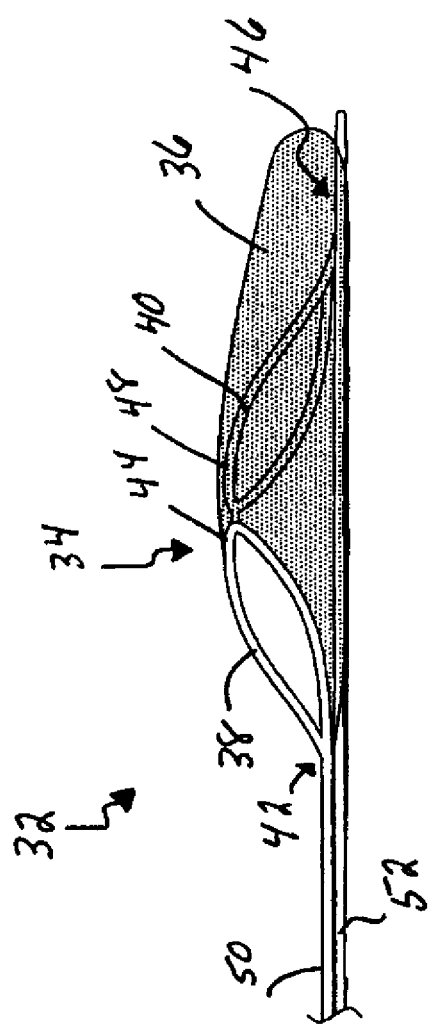
FIG. 2 is a diagrammatic view of a portion of a thrombectomy apparatus in accordance with an embodiment of the invention.

As discussed above, a thrombectomy apparatus may also include a capture basket. FIG. 2 illustrates an expandable capture basket 32 that may, if desired, be used in conjunction with or even incorporated into the thrombectomy catheter 10 discussed with respect to FIG. 1. The expandable capture basket 32 includes a frame structure 34 and a membrane 36 that is disposed over at least a portion of the frame structure 34. In some cases, the membrane 36 may be formed of any suitable material such as those listed above and may be manipulated to have any desired level of porosity. In some cases, the membrane 36 may be constructed to be at least substantially permeable to blood but not to larger items such as thrombi. In some instances, it may be useful to construct the membrane 36 to be at least substantially impermeable to blood flow.

In some cases, the frame structure 34 may include a first loop 38 and a second loop 40. The first loop 38 may have a proximal end 42 and a distal end 44 while the second loop 40 may have a distal end 46 and a proximal end 48. It will be recognized that the first loop 38 may be formed by looping a first length of wire or filament and thus the proximal end 42 may include two wire or filament ends. Similarly, the second loop 40 may be formed by looping a second length of wire or filament and thus the distal end 46 may include two wire or filament ends. In some cases, it is contemplated that the first loop 38 and/or the second loop 40 may instead be formed by welding or otherwise joining together the two ends of the first length of wire or filament to form a closed loop.

Figure 3:
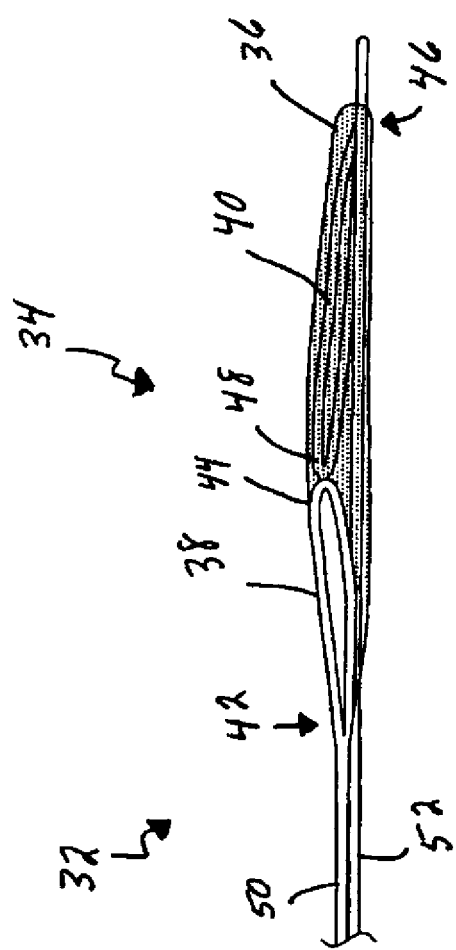
FIG. 3 is a diagrammatic view of a portion of a thrombectomy apparatus in accordance with an embodiment of the invention.
Figure 4:
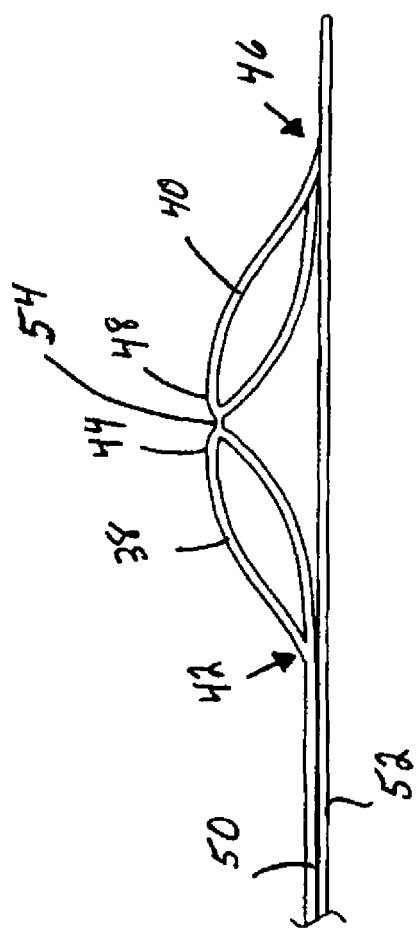
FIG. 4 is a diagrammatic view of a portion of a thrombectomy apparatus in accordance with an embodiment of the invention.

In some instances, the distal end 44 of the first loop 38 may, if desired, be secured to the proximal end 48 of the second loop 40. In some cases, the proximal end 42 of the first loop 38 may extend to and be secured to an actuation filament 50 while the distal end 46 of the second loop 40 may extend to and be secured to a wire 52. It can be seen that the expandable capture basket 32 may be either opened or closed, as desired, by axially moving the actuation filament 50 relative to the wire 52. FIG. 2 shows the expandable capture basket 32 in an open configuration while FIG. 3 shows the expandable capture basket 32 in a closed configuration. FIG. 4 provides a better view of the frame structure 34, as the membrane 36 has been removed.

It will be recognized that structure may be provided to permit the actuation filament 50 to move axially relative to the wire 52 while constraining the actuation filament 50 and/or the wire 52 from excessive radial movement. In some cases, relative movement between the actuation filament 50 and the wire 52 may be controlled by providing at least one of the actuation filament 50 and/or the wire 52 within an appropriate lumen within the thrombectomy catheter 10 (FIG. 1). In some instances, a suitable lumen may be provided either parallel to or even within the evacuation lumen 18, for example.

The actuation filament 50 and the wire 52 may be formed of any suitable material. In some cases, the actuation filament 50 and the wire 52 may, independently, be formed of any suitable polymeric or metallic material. Examples of suitable materials include metal, metal alloy, polymer (some examples of which are disclosed above), a metal-polymer composite, combinations thereof, and the like, or any other suitable material. Some examples of suitable metals and metal alloys include stainless steel, such as 304V, 304L, and 316LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R30035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R30003 such as ELGILOY®, PHYNOX®, and the like); platinum enriched stainless steel; combinations thereof; and the like; or any other suitable material.

As noted above, in some cases the actuation filament 50 and the wire 52 are wire structures. In some instances, however, part or all of the actuation filament 50 and/or the wire 52 may be hollow and may be in fluid communication with a high pressure fluid source such as the high pressure lumen 22 (FIG. 1). In some situations, it may be desirable to have one or more high pressure jets disposed at one or more locations within the frame structure 34. For example, it may be desirable to have a high pressure jet located at a midpoint 54 of the frame structure 34. In some cases, it may be desirable to have one or more high pressure jets disposed along the first loop 38 and/or the second loop 40. In some cases, it is contemplated that the actuation filament 50 and the wire 52 may be wire structures while another feed line (not seen in this Figure) provides fluid to the aforementioned high pressure jets.

Figure 5:
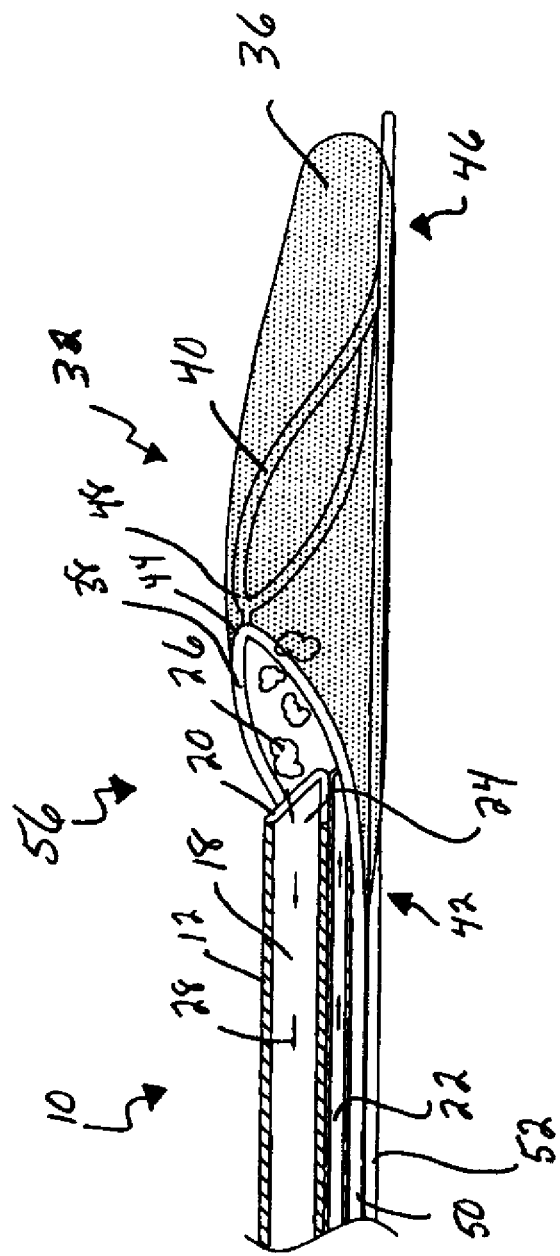
FIG. 5 is a diagrammatic view of a portion of a thrombectomy apparatus in accordance with an embodiment of the invention.

Turning now to FIG. 5, a thrombectomy assembly 56 is shown as including the thrombectomy catheter 10 and the expandable capture basket 32 as previously described. As illustrated, the actuation filament 50 and the wire 52 are shown extending proximally next to the elongate shaft 12. It will be recognized that the elongate shaft 12 may include one or more additional lumens (not illustrated) through which the actuation filament 50 and/or the wire 52 may extend. In some cases, a separate catheter (not shown) may provide a lumen or lumens suitable to constrain the actuation filament 50 and/or the wire 52.

Figure 5A:
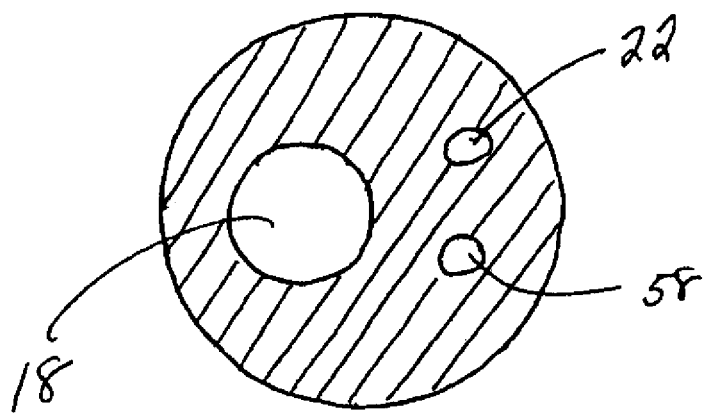
FIG. 5A is a diagrammatic view of a portion of a thrombectomy apparatus in accordance with an embodiment of the invention.
Figure 5B:
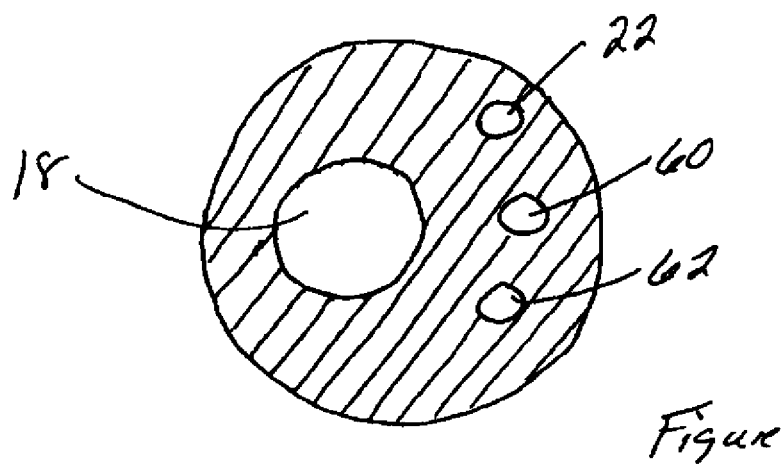
FIG. 5B is a diagrammatic view of a portion of a thrombectomy apparatus in accordance with an embodiment of the invention.

FIGS. 5A and 5B are schematic cross-sectional views providing several examples of how the elongate shaft 12 could accommodate the actuation filament 50 and the wire 52. FIG. 5A provides an example in a wire lumen 58 extends through the elongate shaft 12 and is parallel with the evacuation lumen 18 and the high pressure lumen 22. The wire lumen 58 may be sized to accommodate both the actuation filament 50 and the wire 52. In some instances, the wire lumen 58 may have a diameter that is large enough to permit relative axial movement between the actuation filament 50 and the wire 52 yet small enough to limit relative radial movement between the actuation filament 50 and the wire 52.

FIG. 5B provides an example in which an actuation filament lumen 60 and a wire lumen 62 extend through the elongate shaft 12 and are parallel with the evacuation lumen 18 and the high pressure lumen 22. The actuation filament lumen 60 may be sized to slidingly accommodate the actuation filament 50 and the wire lumen 62 may be sized to slidingly accommodate the wire 52. While FIGS. 5A and 5B show the additional lumens as being formed within a single shaft, it will be recognized that one or more of wire lumen 58, actuation filament lumen 60 and wire lumen 62 may be formed within distinct and separate tubular members that may be joined together to form the elongate shaft 12.

Figure 6:
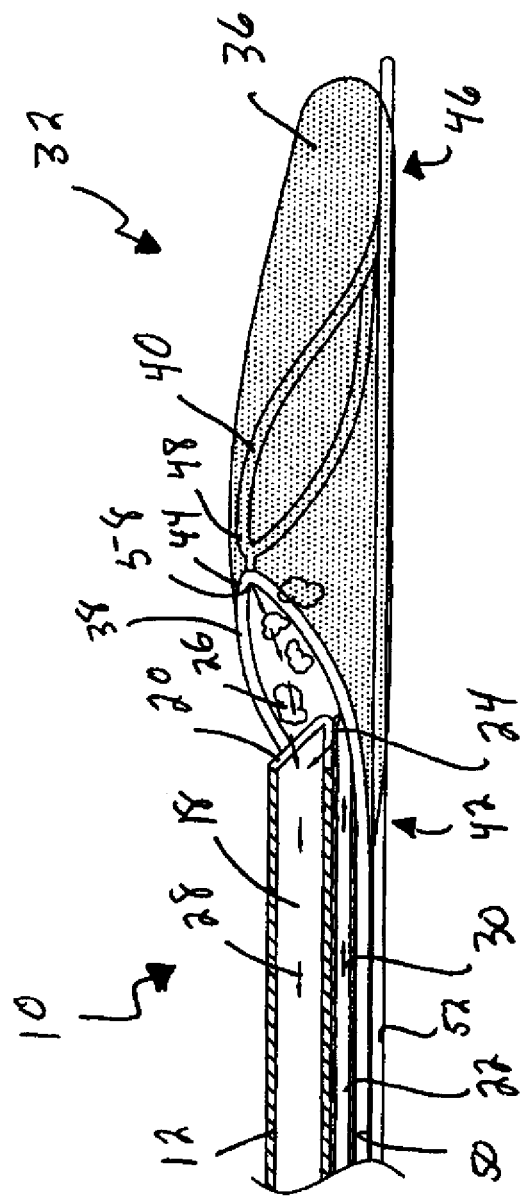
FIG. 6 is a diagrammatic view of a portion of a thrombectomy apparatus in accordance with an embodiment of the invention.

FIG. 6 is similar to FIG. 5, but adds a high pressure jet 58 located near the distal end 44 of the first loop 38. In some cases, the high pressure jet 58 may simply be a small aperture formed within a tube forming the first loop 38, particularly if the tube forming the first loop 38 is hollow and is in fluid communication with a high pressure fluid source such as the high pressure lumen 22. In some instances, it is contemplated that the high pressure jet 58 may be an orifice provided in a separate fluid line (not illustrated).

As illustrated, the high pressure jet 58 may be considered as being pointed at least partially towards the distal opening 20 of the evacuation lumen 18. In some cases, the high pressure jet 58 may be pointed in a more downward direction. In some instances, the high pressure jet 58 may be aimed more directly at an interior surface of the membrane 36. In some cases, two, three or more high pressure jets such as high pressure jet 58 may be disposed at various locations in and near the expandable capture basket 32.

Figure 7:
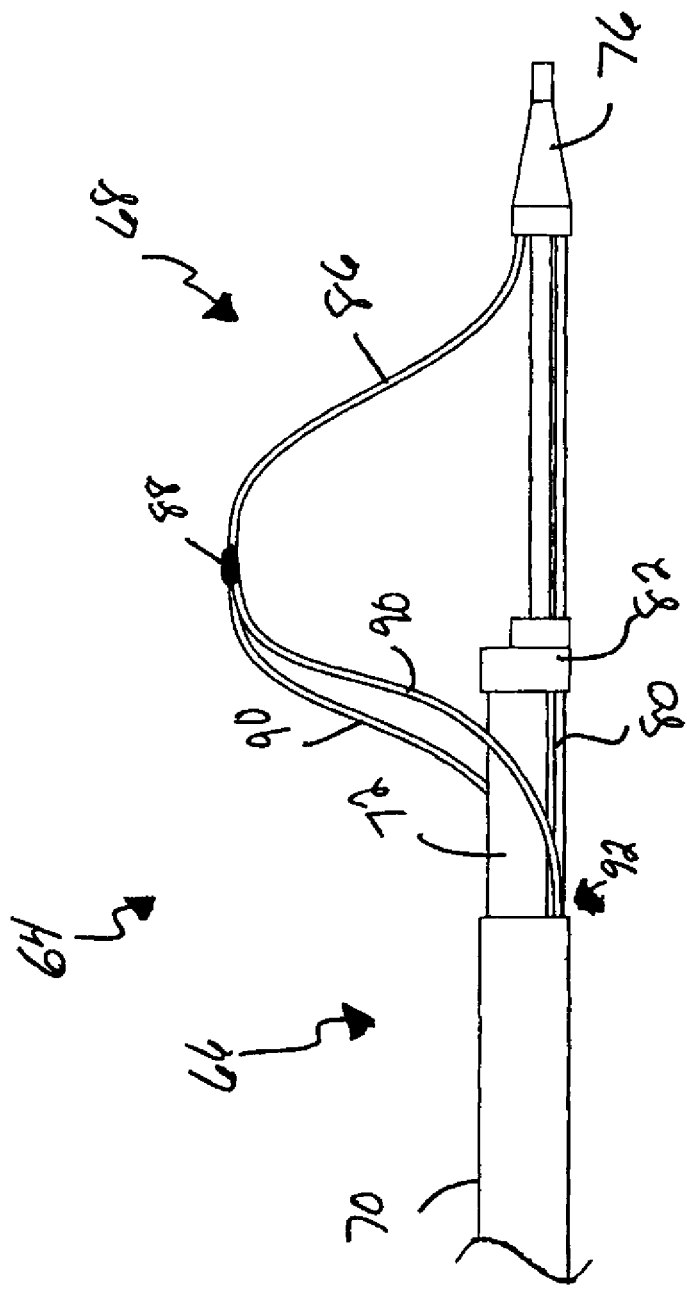
FIG. 7 is a diagrammatic view of a portion of a thrombectomy apparatus in accordance with an embodiment of the invention.

FIG. 7 provides an illustrative thrombectomy apparatus 64 that is configured to provide pressurized fluid to one or more locations within a capture basket. The thrombectomy apparatus 64 includes a catheter portion 66 and a basket portion 68. The catheter portion 66 includes a proximal shaft section 70 and an intermediate shaft section 72 that is disposed at least partially within the proximal shaft section 70 and extends distally therefrom. A distal shaft section 74 extends from the intermediate shaft section 72 and extends distally to a distal tip 76. It will be recognized that the catheter portion 66 may include one or more lumens such as an evacuation lumen, a high pressure fluid lumen, wire lumen, guidewire lumen, and the like.

The proximal shaft section 70 and the intermediate shaft section 72 may be configured to provide an evacuation lumen similar to the evacuation lumen 18 previously discussed. An evacuation lumen may, for example, terminate at a distal opening 78. As discussed previously, the evacuation lumen (not seen in this view) may be placed in fluid communication with a low pressure source such as suction to draw thrombi and other unwanted material into the evacuation lumen.

A proximal high pressure fluid line 80 may extend parallel to the intermediate shaft section 72. The proximal high pressure fluid line 80 may extend proximally within the proximal shaft section and may be in fluid communication with a high pressure fluid source. The proximal high pressure fluid line 80 may extend to a junction 82, from which a distal high pressure fluid line 84 may extend distally to the distal tip 76. If desired, the junction 82 may include a jet orifice, but this is not required.

For clarity, the basket portion 68 is shown without a membrane, but it will be recognized that the basket portion 68 may include a membrane similar to the membrane 36 described previously with respect to FIG. 2. The basket portion 68 includes a tubular line 86 that extends proximally from the distal tip 76. In some instances, the distal tip 76 may include appropriate plumbing connections such that the tubular line 86 may be in fluid communication with the distal high pressure fluid line 84. In some cases, the tubular line 86 may extend to a junction 88. If desired, the junction 88 may also include a jet orifice.

A pair of actuation filaments 90 are connected to the junction 88 and extend proximally therefrom. In some cases, the actuation filaments 90 enter the proximal shaft section 70 via an entrance 92 and extend proximally through the proximal shaft section 90. By moving the actuation filaments 90 in an axial direction, the basket portion 68 may be moved between an open configuration (as illustrated) and a closed configuration. In some instances, the actuation filaments 90 may be wires. In some cases, one or both of the actuation filaments 90 may be hollow tubes that may be in fluid communication with the junction 88.

FIGS. 8 through 13 provide illustrative but non-limiting examples of thrombectomy apparatuses. For clarity, certain elements such as wire lumens and capture basket membranes are excluded from the drawings. It will be recognized, however, that these elements may be included, as desired.

Figure 8:
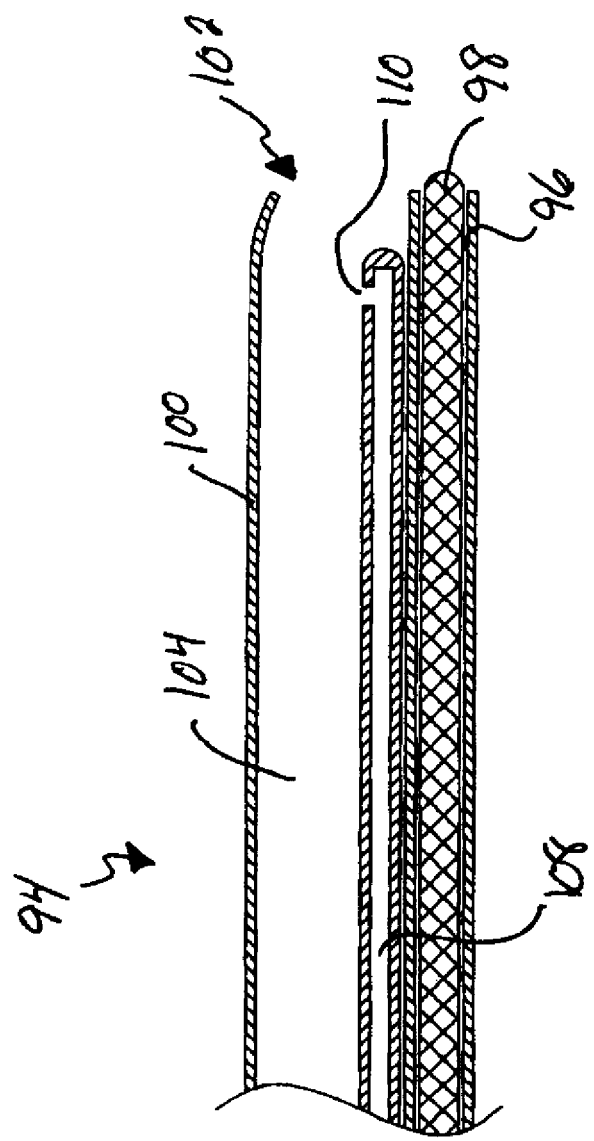
FIG. 8 is a diagrammatic view of a portion of a thrombectomy apparatus in accordance with an embodiment of the invention.

FIG. 8 shows a thrombectomy apparatus 94 that may be either a monorail or an over-the-wire type. The thrombectomy apparatus 94 includes a guidewire lumen 96 through which a guidewire 98 is disposed. While only a distal portion of the guidewire lumen 96 is seen in the Figure, one of skill will recognize that the guidewire lumen 96 may have a relatively short length if the thrombectomy apparatus 94 is intended as a monorail (or single-operator exchange) catheter. In some instances, the guidewire lumen 96 may extend a substantial distance proximally if the thrombectomy apparatus 94 is designed as an over-the-wire catheter.

The thrombectomy apparatus 94 includes an elongate shaft 100 extending to a distal end 102. The guidewire lumen 96 may, if desired, be formed as an integral portion of the elongate shaft 100. An evacuation lumen 104 is formed within the elongate shaft 100 and extends distally to a distal opening 106. The evacuation lumen 104 may be in fluid communication with a low pressure source such as vacuum. In some instances, as illustrated, the distal opening 106 may be tapered to facilitate advancement of the thrombectomy apparatus 94 through a patient's vasculature, for example, yet still be sized appropriate to accommodate thrombi and other similar material.

The elongate shaft 100 also includes a high pressure lumen 108 that extends distally within the elongate shaft 100. The high pressure lumen 108 includes a jet orifice 110 that is disposed in a side of the high pressure lumen 108 proximate a distal end thereof. It can be seen that in this configuration, the jet orifice 110 may provide a fluid jet that traverses the evacuation lumen 104 and thus may help break up any thrombi passing into the evacuation lumen 104.

Figure 9:
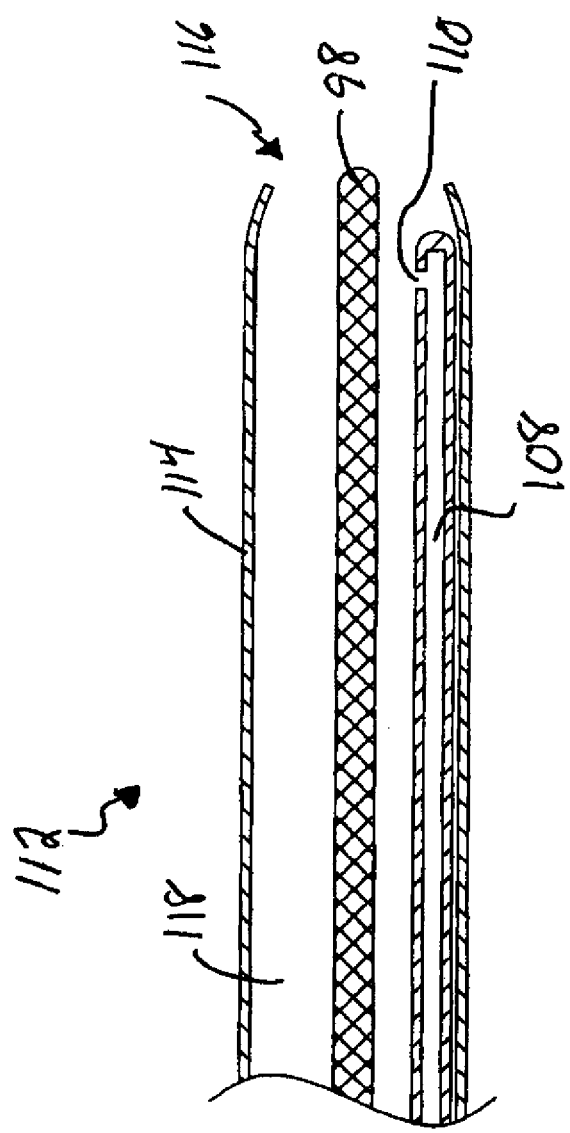
FIG. 9 is a diagrammatic view of a portion of a thrombectomy apparatus in accordance with an embodiment of the invention.

FIG. 9 shows a thrombectomy apparatus 112 that is configured as an over-the-wire type. The thrombectomy apparatus 112 includes an elongate shaft 114 extending to a distal end 116. An evacuation lumen 118 is formed within the elongate shaft 114 and extends distally to a distal opening 120. A guidewire 98 extends through the evacuation lumen 118.

The evacuation lumen 118 may be in fluid communication with a low pressure source such as vacuum. In some instances, as illustrated, the distal opening 120 may be tapered to facilitate advancement of the thrombectomy apparatus 112 through a patient's vasculature, for example, yet still be sized appropriate to accommodate thrombi and other similar material.

The elongate shaft 101140 also includes a high pressure lumen 108 that extends distally within the elongate shaft 100. The high pressure lumen 108 includes a jet orifice 110 that is disposed in a side of the high pressure lumen 108 proximate a distal end thereof. It can be seen that in this configuration, the jet orifice 110 may provide a fluid jet that traverses the evacuation lumen 118 and thus may help break up any thrombi passing into the evacuation lumen 118.

Figure 10:
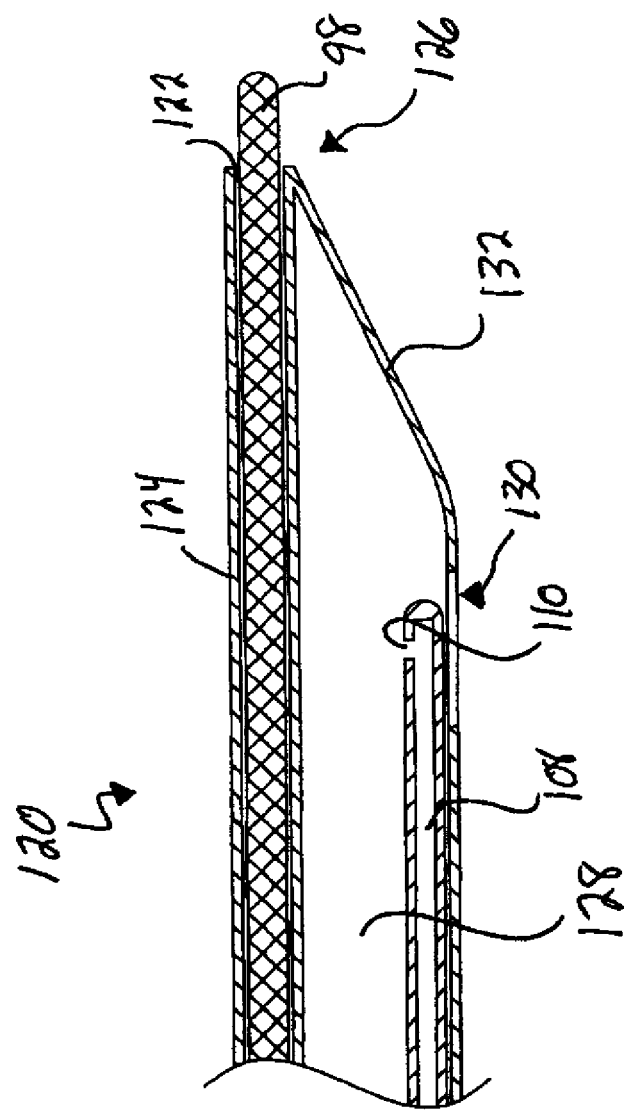
FIG. 10 is a diagrammatic view of a portion of a thrombectomy apparatus in accordance with an embodiment of the invention.

FIG. 10 shows a thrombectomy apparatus 120 that may be either a monorail or an over-the-wire type. The thrombectomy apparatus 120 includes a guidewire lumen 122 through which a guidewire 98 is disposed. While only a distal portion of the guidewire lumen 122 is seen in the Figure, one of skill will recognize that the guidewire lumen 122 may have a relatively short length if the thrombectomy apparatus 120 is intended as a monorail (or single-operator exchange) catheter. In some instances, the guidewire lumen 122 may extend a substantial distance proximally if the thrombectomy apparatus 120 is designed as an over-the-wire catheter.

The thrombectomy apparatus 120 includes an elongate shaft 124 extending to a distal end 126. The guidewire lumen 122 may, if desired, be formed as an integral portion of the elongate shaft 124. An evacuation lumen 128 is formed within the elongate shaft 124 and extends distally. In some cases, as illustrated, the evacuation lumen 128 may have a side opening 130 that is sized to permit thrombi and similar material to enter the evacuation lumen 128 through the side opening 130. The evacuation lumen 128 may be in fluid communication with a low pressure source such as vacuum. In some instances, as illustrated, the elongate shaft 124 may terminate in an angled end 132 to facilitate advancement of the thrombectomy apparatus 120 through a patient's vasculature, for example.

The elongate shaft 124 also includes a high pressure lumen 108 that extends distally within the elongate shaft 124. The high pressure lumen 108 includes a jet orifice 110 that is disposed in a side of the high pressure lumen 108 proximate a distal end thereof. It can be seen that in this configuration, the jet orifice 110 may provide a fluid jet that traverses the evacuation lumen 128 and thus may help break up any thrombi passing into the evacuation lumen 128. In this configuration, the jet orifice 110 may be positioned at or near a midpoint of the side opening 130.

Figure 11:
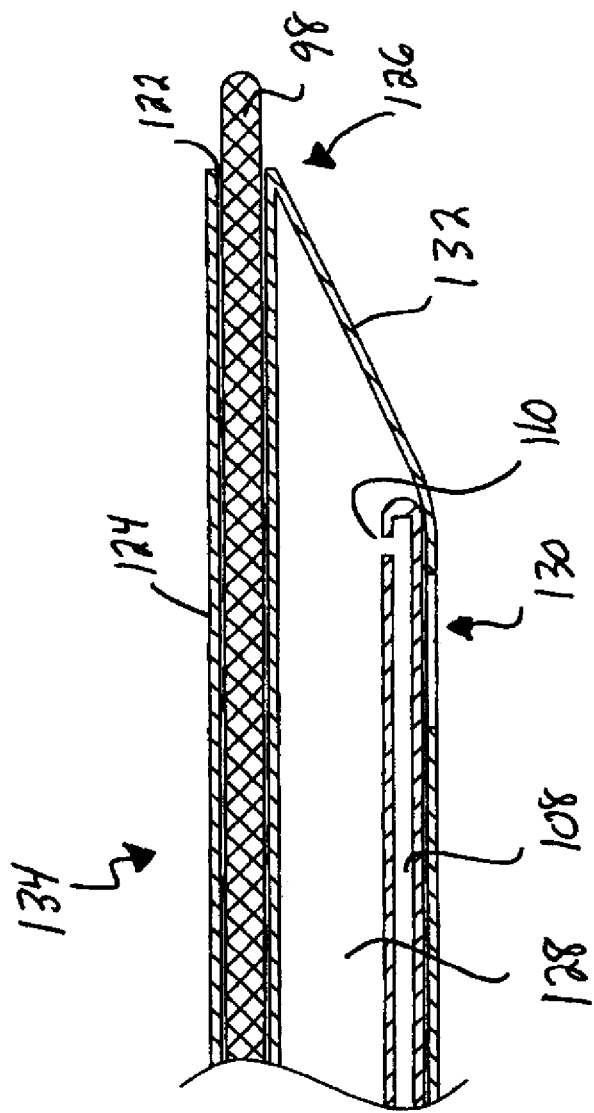
FIG. 11 is a diagrammatic view of a portion of a thrombectomy apparatus in accordance with an embodiment of the invention.

FIG. 11 shows a thrombectomy apparatus 134 that may be either a monorail or an over-the-wire type. The thrombectomy apparatus 134 includes a guidewire lumen 122 through which a guidewire 98 is disposed. While only a distal portion of the guidewire lumen 122 is seen in the Figure, it will be recognized that the guidewire lumen 122 may have a relatively short length if the thrombectomy apparatus 134 is intended as a monorail (or single-operator exchange) catheter. In some instances, the guidewire lumen 122 may extend a substantial distance proximally if the thrombectomy apparatus 134 is designed as an over-the-wire catheter.

The thrombectomy apparatus 134 includes an elongate shaft 124 extending to a distal end 126. The guidewire lumen 122 may, if desired, be formed as an integral portion of the elongate shaft 124. An evacuation lumen 128 is formed within the elongate shaft 124 and extends distally. In some cases, as illustrated, the evacuation lumen 128 may have a side opening 130 that is sized to permit thrombi and similar material to enter the evacuation lumen 128 through the side opening 130. The evacuation lumen 128 may be in fluid communication with a low pressure source such as vacuum. In some instances, as illustrated, the elongate shaft 124 may terminate in an angled end 132 to facilitate advancement of the thrombectomy apparatus 134 through a patient's vasculature, for example.

The elongate shaft 124 also includes a high pressure lumen 108 that extends distally within the elongate shaft 124. The high pressure lumen 108 includes a jet orifice 110 that is disposed in a side of the high pressure lumen 108 proximate a distal end thereof. In this configuration, the jet orifice 110 may be positioned at or near a distal edge of the side opening 130.

Figure 12:
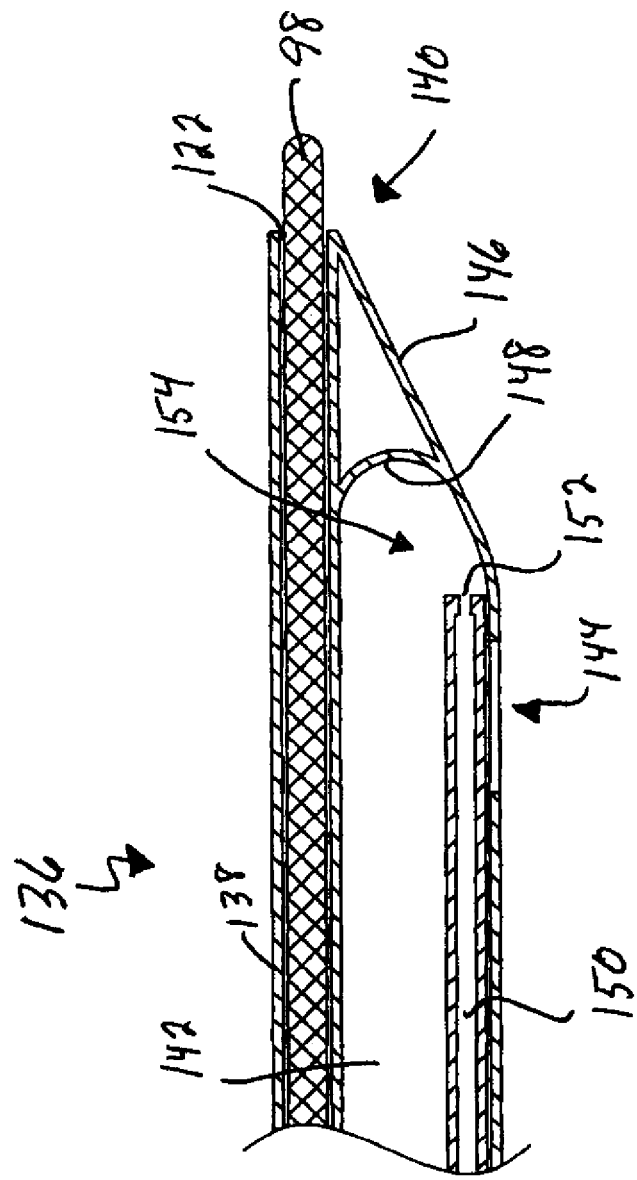
FIG. 12 is a diagrammatic view of a portion of a thrombectomy apparatus in accordance with an embodiment of the invention.

FIG. 12 shows a thrombectomy apparatus 136 that may be either a monorail or an over-the-wire type. The thrombectomy apparatus 136 includes a guidewire lumen 122 through which a guidewire 98 is disposed. While only a distal portion of the guidewire lumen 122 is seen in the Figure, one of skill will recognize that the guidewire lumen 122 may have a relatively short length if the thrombectomy apparatus 136 is intended as a monorail (or single-operator exchange) catheter. In some instances, the guidewire lumen 122 may extend a substantial distance proximally if the thrombectomy apparatus 136 is designed as an over-the-wire catheter.

The thrombectomy apparatus 136 includes an elongate shaft 138 extending to a distal end 140. The guidewire lumen 122 may, if desired, be formed as an integral portion of the elongate shaft 124. An evacuation lumen 142 is formed within the elongate shaft 124 and extends distally. In some cases, as illustrated, the evacuation lumen 142 may have a side opening 144 that is sized to permit thrombi and similar material to enter the evacuation lumen 142 through the side opening 144. The evacuation lumen 142 may be in fluid communication with a low pressure source such as vacuum. In some instances, as illustrated, the elongate shaft 138 may terminate in an angled end 146 to facilitate advancement of the thrombectomy apparatus 136 through a patient's vasculature, for example. In some cases, the angled end 146 may include an interior curved surface 148, if desired to control flow characteristics within the evacuation lumen 142.

The elongate shaft 138 also includes a high pressure lumen 150 that extends distally within the elongate shaft 138. The high pressure lumen 150 includes a jet orifice 152 that is disposed in a distal end of the high pressure lumen 150. It can be seen that in this configuration, the jet 152 110 may provide a fluid jet that can cause turbulence within a distal region 154 of the evacuation lumen 142. In some cases, this turbulence may help break up any thrombi passing into the evacuation lumen 142.

Figure 13:
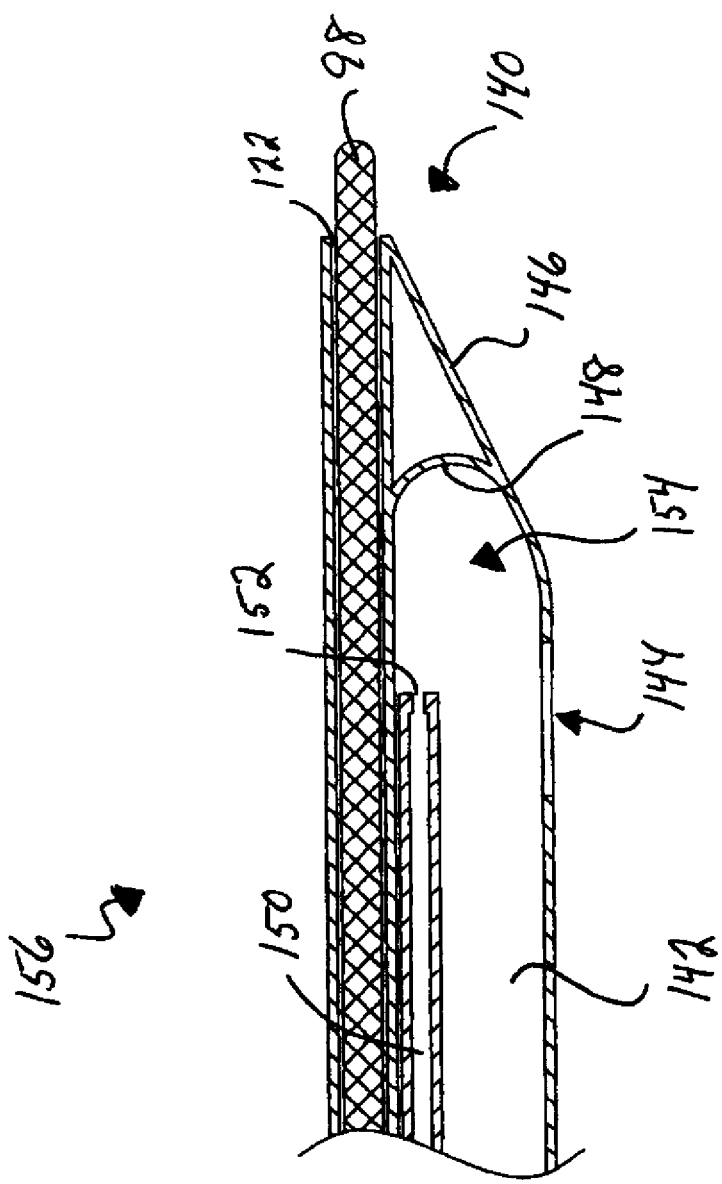
FIG. 13 is a diagrammatic view of a portion of a thrombectomy apparatus in accordance with an embodiment of the invention.

FIG. 13 shows a thrombectomy apparatus 156 that may be either a monorail or an over-the-wire type. The thrombectomy apparatus 156 includes a guidewire lumen 122 through which a guidewire 98 is disposed. While only a distal portion of the guidewire lumen 122 is seen in the Figure, one of skill will recognize that the guidewire lumen 122 may have a relatively short length if the thrombectomy apparatus 156 is intended as a monorail (or single-operator exchange) catheter. In some instances, the guidewire lumen 122 may extend a substantial distance proximally if the thrombectomy apparatus 156 is designed as an over-the-wire catheter.

The thrombectomy apparatus 156 includes an elongate shaft 138 extending to a distal end 140. The guidewire lumen 122 may, if desired, be formed as an integral portion of the elongate shaft 124. An evacuation lumen 142 is formed within the elongate shaft 124 and extends distally. In some cases, as illustrated, the evacuation lumen 142 may have a side opening 144 that is sized to permit thrombi and similar material to enter the evacuation lumen 142 through the side opening 144. The evacuation lumen 142 may be in fluid communication with a low pressure source such as vacuum. In some instances, as illustrated, the elongate shaft 138 may terminate in an angled end 146 to facilitate advancement of the thrombectomy apparatus 156 through a patient's vasculature, for example. In some cases, the angled end 146 may include an interior curved surface 148, if desired to control flow characteristics within the evacuation lumen 142.

The elongate shaft 138 also includes a high pressure lumen 150 that extends distally within the elongate shaft 138. Unlike FIG. 12, in FIG. 13 the high pressure lumen 150 is located away from the side opening 144. The high pressure lumen 150 includes a jet orifice 152 that is disposed in a distal end of the high pressure lumen 150. It can be seen that in this configuration, the jet 152 110 may provide a fluid jet that can cause turbulence within a distal region 154 of the evacuation lumen 142. In some cases, this turbulence may help break up any thrombi passing into the evacuation lumen 142.

Figure 14:
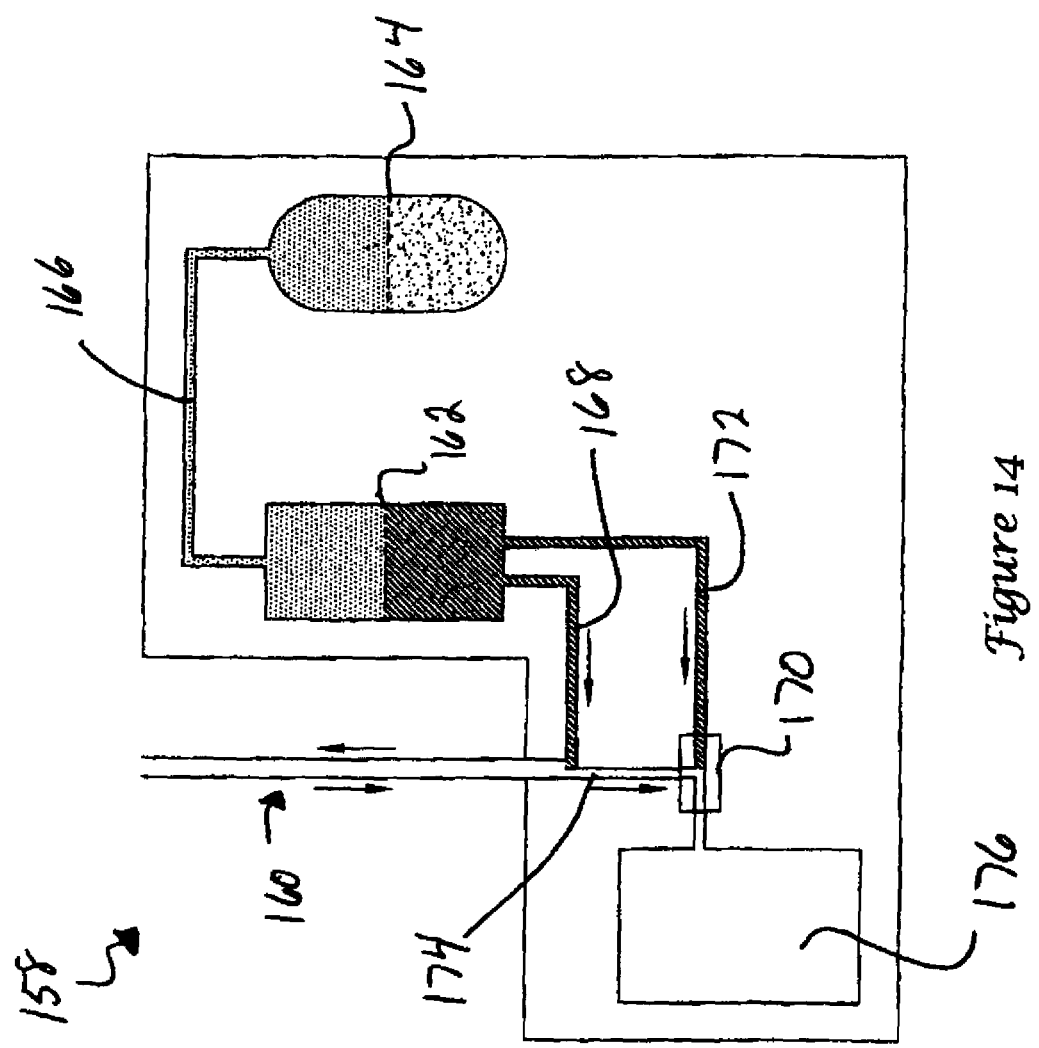
FIG. 14 is a diagrammatic view of a thrombectomy system in accordance with an embodiment of the invention.

FIG. 14 schematically illustrates a thrombectomy system 158. In some cases, the thrombectomy system 158 may be considered as being a self-contained assembly that can be operated without exterior fluid or power connections. The thrombectomy system 158 includes a thrombectomy apparatus 160, similar to those described above with respect to FIGS. 1 through 13. A working fluid reservoir 162 may be pressurized via a propellant that is stored within a propellant reservoir 164.

In some cases, the propellant reservoir 164 may contain a propellant in liquid form. As the propellant vaporizes, the resultant gas may travel through a line 166 and into the working fluid reservoir 162. As diagrammatically illustrated, the propellant reservoir 164 may be about half full with a liquefied propellant (bottom half as drawn) and about half full with a vaporized propellant. Similarly, the bottom half of the working fluid reservoir 162 may be filled with a liquid working fluid such as saline while the top half is filled with the vaporized propellant. In some cases, the propellant is carbon dioxide. As a result, the working fluid in working fluid reservoir 162 is pressurized as the propellant in propellant reservoir 164 vaporizes. Alternatively, it is contemplated that the working fluid may be pressurized externally. For example, an external source of a pressurized gas such as oxygen or nitrogen could be used to pressure the working fluid within the working fluid reservoir 162.

Pressurized working fluid may be provided to the thrombectomy apparatus 160 via a supply line 168. In some cases, pressurized working fluid may also be provided to a suction device 170 via another supply line 172. The suction device 170 may, for example, be a jet pump suction device, a venture, or the like, and may be connected to a low pressure lumen within the thrombectomy apparatus 160 via supply line 174. In some cases, it is contemplated that suction may instead be provided externally, such as a vacuum port within a hospital room, for example. Any thrombi or other material removed via the thrombectomy apparatus 160 may be collected in a collection reservoir 176. In some cases, the collection reservoir 176 may be a reusable container. In some instances, the collection reservoir 176 may be a disposable bag or other similar structure.

Figure 15:
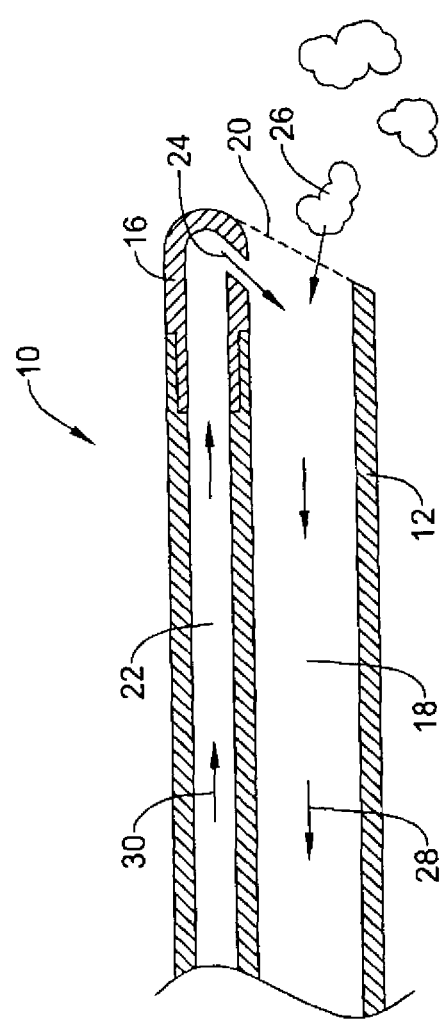
FIG. 15 is a diagrammatic view of a thrombectomy system in accordance with an embodiment of the invention.

FIG. 15 shows a thrombectomy apparatus which may function without an associated capture device. Thrombectomy catheter 10 includes an elongate shaft 12 having an evacuation lumen 18 and a generally parallel high pressure lumen 22. The elongate shaft 12 optionally may accommodate the high pressure lumen 22, a guide wire lumen (not shown) and the like as shown in FIG. 5A. In other embodiments, the high pressure lumen 22 may be provided as a distinct and separate tubular member that may be joined to the evacuation lumen 18 to form elongate shaft 12. The evacuation lumen 18 may terminate at a distal opening 20. The high pressure lumen 22 may terminate near the distal opening 20 of elongate shaft 12 at a distal opening 24. In some embodiments, the distal opening 24 may be formed in a distal plug 16 inserted in the high pressure lumen 22. Thrombi 26, generically shown disposed just distal of the distal opening 20 of elongate shaft 12, may be drawn into evacuation lumen 18 by providing a low pressure source to a proximal end (not illustrated) of the evacuation lumen 18. In some embodiments a suitable fluid such as a saline or other therapeutically acceptable fluid may travel in a direction indicated by arrow 30 within high pressure lumen 22. Upon exiting distal opening 24, the flow may join a flow existing within evacuation lumen 18 generally in the direction of arrow 28. In some configurations, especially when the flow exiting distal opening 24 is directed generally between perpendicular to the axis of the low pressure lumen 18 and axially within the low pressure lumen in the direction indicated by arrow 30, the flow exiting distal opening 24 may provide an ejector/aspirator action to assist in drawing thrombus 26 within elongate shaft 12. It is believed that the flow exiting distal opening 24 may disrupt and dilute thrombus as it enters evacuation lumen 18.

In some cases, parts or all of the devices described herein may be doped with, made of, coated with, or otherwise include a radiopaque material. Radiopaque materials are understood to be materials capable of producing a relatively bright image on a fluoroscopy screen or another imaging technique during a medical procedure. Some examples of radiopaque materials can include, but are not limited to, gold, platinum, palladium, tantalum, tungsten alloy, polymer material loaded with a radiopaque filler, and the like.

In some instances, a degree of MRI compatibility may be imparted into parts of the devices described herein. For example, to enhance compatibility with Magnetic Resonance Imaging (MRI) machines, it may be desirable to make various portions of the devices described herein from materials that do not substantially distort MRI images or cause substantial artifacts (gaps in the images). Some ferromagnetic materials, for example, may not be suitable as they may create artifacts in an MRI image. In some cases, the devices described herein may include materials that the MRI machine can image. Some materials that exhibit these characteristics include, for example, tungsten, cobalt-chromium-molybdenum alloys (e.g., UNS: R30003 such as ELGILOY®, PHYNOX®, and the like), nickel-cobalt-chromium-molybdenum alloys (e.g., UNS: R30035 such as MP35-N® and the like), nitinol, and the like, and others.

In some instances, some of the devices described herein may include a coating such as a lubricious coating or a hydrophilic coating. Hydrophobic coatings such as fluoropolymers provide a dry lubricity. Lubricious coatings improve steerability and improve lesion crossing capability. Suitable lubricious polymers are well known in the art and may include silicone and the like, hydrophilic polymers such as high-density polyethylene (HDPE), polytetrafluoroethylene (PTFE), polyarylene oxides, polyvinylpyrolidones, polyvinylalcohols, hydroxy alkyl cellulosics, algins, saccharides, caprolactones, and the like, and mixtures and combinations thereof. Hydrophilic polymers may be blended among themselves or with formulated amounts of water insoluble compounds (including some polymers) to yield coatings with suitable lubricity, bonding, and solubility.

It should be understood that this disclosure is, in many respects, only illustrative. Changes may be made in details, particularly in matters of shape, size, and arrangement of steps without exceeding the scope of the invention. The scope of the invention is, of course, defined in the language in which the appended claims are expressed.

What is claimed is:

1. A method of performing a thrombectomy, comprising:
   inserting an elongate catheter shaft into a patient's vasculature, the elongate catheter shaft comprising a low pressure lumen comprising a proximal end and a distal end, the distal end forming an opening, the elongate catheter shaft further comprising a high pressure lumen comprising a proximal end and a distal end, the high pressure lumen extending within the low pressure lumen, wherein the high pressure lumen is closed at its distal end by a plug inserted into the high pressure lumen, and wherein the high pressure lumen comprises an opening disposed near its distal end which communicates between the high pressure lumen and the low pressure lumen, and which is in proximity to the opening of the low pressure lumen;
   advancing the elongate catheter shaft to a target site in the vasculature;
   providing a flow of fluid through the high pressure lumen from a high pressure source such that the fluid exits from the opening of the high pressure lumen to break a thrombus within the low pressure lumen into smaller pieces when the proximal end of the low pressure lumen is coupled to a vacuum source; and
   providing a vacuum through the low pressure lumen from the vacuum source to aspirate the thrombus via the low pressure lumen.

2. The method of claim 1, wherein the flow of fluid exiting the opening of the high pressure lumen is substantially perpendicular to a longitudinal axis of the elongate catheter shaft.

3. The method of claim 1, wherein the flow of fluid exiting the opening of the high pressure lumen is obliquely oriented to a longitudinal axis of the elongate catheter shaft.

4. The method of claim 1, wherein the flow of fluid exiting the opening of the high pressure lumen is directed generally between perpendicular to a longitudinal axis of the low pressure lumen and axially proximally within the low pressure lumen.

5. The method of claim 1, further comprising advancing a guidewire to the target site in the vasculature.

6. The method of claim 5, wherein advancing a guidewire to the target site in the vasculature comprises advancing the guidewire through a guidewire lumen of the elongate catheter shaft.

7. The method of claim 1, wherein the flow of fluid comprises at least one jet.

8. The method of claim 1, wherein the flow of fluid comprises a plurality of jets.

9. The method of claim 1, wherein the flow of fluid contacts a sidewall of the low pressure lumen.

10. The method of claim 1, wherein the fluid comprises saline.

11. The method of claim 1, wherein the flow of fluid causes turbulence within the low pressure lumen.

12. The method of claim 1, further comprising collecting the thrombus in a collection reservoir in fluid communication with the low pressure lumen.

13. A method of performing a thrombectomy, comprising:
   inserting an elongate catheter shaft into a patient's vasculature, the elongate catheter shaft comprising a low pressure lumen comprising a proximal end and a distal end, the distal end forming an opening, the elongate catheter shaft further comprising a high pressure lumen comprising a proximal end and a distal end, wherein the high pressure lumen is closed at its distal end by a plug inserted into the high pressure lumen, and wherein the high pressure lumen comprises a sidewall opening disposed near its distal end which opens into the low pressure lumen;
   advancing the elongate catheter shaft to a target site in the vasculature;
   providing a flow of fluid through the high pressure lumen from a high pressure source when the proximal end of the low pressure lumen is coupled to a vacuum source, such that the fluid exits from the opening of the high pressure lumen at least partially breaks apart a thrombus within the low pressure lumen, wherein the fluid is directed generally between perpendicular to a longitudinal axis of the low pressure lumen and axially proximally within the low pressure lumen; and
   providing a vacuum through the low pressure lumen, the low pressure lumen in fluid communication with the vacuum source to aspirate the thrombus via the low pressure lumen.

14. The method of claim 13, further comprising advancing a guidewire to the target site in the vasculature.

15. The method of claim 14, wherein advancing a guidewire to the target site in the vasculature comprises advancing the guidewire through a guidewire lumen of the elongate catheter shaft.

16. The method of claim 13, wherein the flow of fluid comprises at least one jet.

17. The method of claim 13, wherein the flow of fluid comprises a plurality of jets.

18. The method of claim 13, wherein the fluid comprises saline.

19. The method of claim 13, wherein the flow of fluid causes turbulence within the low pressure lumen.

20. The method of claim 13, further comprising collecting the thrombus in a collection reservoir in fluid communication with the low pressure lumen.

\* \* \* \* \*